United States Patent
Williams et al.

(10) Patent No.: US 7,691,890 B2
(45) Date of Patent: Apr. 6, 2010

(54) ANTI-VIRAL USES OF LEFLUNOMIDE PRODUCTS

(75) Inventors: James W. Williams, 655 Superior, Oak Park, IL (US) 60302; Anita Chong, Chicago, IL (US); W. James Waldman, Dublin, OH (US)

(73) Assignee: James W. Williams, Chicago, IL (US)

( * ) Notice: Subject to any disclaimer, the term of this patent is extended or adjusted under 35 U.S.C. 154(b) by 594 days.

(21) Appl. No.: 09/529,053

(22) PCT Filed: Mar. 11, 1999

(86) PCT No.: PCT/US99/05326

§ 371 (c)(1), (2), (4) Date: Apr. 6, 2000

(87) PCT Pub. No.: WO99/45908

PCT Pub. Date: Sep. 16, 1999

(65) Prior Publication Data

US 2003/0114507 A1 Jun. 19, 2003

Related U.S. Application Data

(60) Provisional application No. 60/077,552, filed on Mar. 11, 1998.

(51) Int. Cl.
A61K 31/42 (2006.01)
A61K 31/505 (2006.01)
A61K 31/70 (2006.01)
A61K 31/16 (2006.01)

(52) U.S. Cl. .......... 514/378; 514/269; 514/49; 514/50; 514/51; 514/613; 514/626

(58) Field of Classification Search .......... 514/378, 514/269, 49–51
See application file for complete search history.

(56) References Cited

U.S. PATENT DOCUMENTS

| | | | | |
|---|---|---|---|---|
| 4,087,535 | A | 5/1978 | Heubach | 424/272 |
| 4,351,841 | A | 9/1982 | Kämmerer et al. | 424/272 |
| 4,965,276 | A | 10/1990 | Bartlett et al. | 514/378 |
| 5,519,042 | A | 5/1996 | Morris et al. | 514/378 |
| 5,556,870 | A * | 9/1996 | Weithmann et al. | 514/378 |

FOREIGN PATENT DOCUMENTS

| | | |
|---|---|---|
| EP | 0 607 775 | 7/1994 |
| EP | 0 607 776 | 7/1994 |
| WO | 94/24095 | 10/1994 |
| WO | WO 94/24095 * | 10/1994 |

(Continued)

OTHER PUBLICATIONS

CAPLUS Abstract, AN 1991:581163, 1991 Flamand et al.*

(Continued)

Primary Examiner—Shengjun Wang
(74) Attorney, Agent, or Firm—Marshall, Gerstein & Borun LLP

(57) ABSTRACT

The present invention relates to anti-viral uses of leflunomide product, alone or in combination with other anti-viral agents, or in combination with a pyrimidine such as uridine.

11 Claims, 9 Drawing Sheets

FOREIGN PATENT DOCUMENTS

WO 98/42338 1/1998

OTHER PUBLICATIONS

Hammer, 'Advances in antiretroviral therapy and viral load monitoring' 1996, AIDS vol. 10, suppl 3, p. s1-s11.*
McChesney et al. 'An evaluation of leflunomide in the canine renal transplantation model' 1994, Transplantation, vol. 57, No. 12 p. 1717-1722.*
Flamand et al. Human herpes virus 6 induces interleukin-1 beta and tumor necrosis factor alpha, but not interleukin-1 beta, in peripheral blood mononuclear cell cultures, J. virology, 1995, vol. 65, No. 9, pp. 5105-5110.*
Colacino "Mechanisms for the anti-hepatitis B virus activity and mitochondrial toxicity of fialuridine (FIAU)," Antiviral Research, 1996, vol. 29, pp. 125-139.*
Lim, J.K., et al., "Analgesic, Anti-inflammatory and Antiviral Effects of Melandrin Derivatives," *Yakhak Hoeji*, vol. 38, No. 3, 345-350 (1994).
McChesney, L.P., et al., "An Evaluation of Leflunomide in the Canine renal transplantation model," *Transplantation*, vol. 57, No. 12, 1717 (1994).
Waldman, W.J., et al., "Inhibition of Cytomegalovirus by the Immunosuppressive Agent Leflunomide," *Faseb Journal*, vol. 12, No. 5, A808 (1998).
Waldman, W.J. et al., "Inhibition of Cytomegalovirus in vitro and in vivo by the Experimental Immunosuppressive Agent Leflunomide," *Transplantation*, vol. 67, No. 7, 825 (1999) reprint.
International Search Report for PCT/US99/05326 mailed Sep. 12, 1999.
Johnson, et al., "Inhibitory Effect of 4-(4-fluorophenyl)-2-(4-hydroxyphenyl)-5-(4-pyridyl) 1H-imidazole on HCMV DNA Replication and Permissive Infection," *Antiviral Research*, 41:101-111 (1999).
Kim, et al., "Studies on the Antiviral Activity of Protein Kinase Inhibitors against the Replication of Vesicular Stomatitis Virus," *Biol. Pharm. Bull.*, 18(6): 895-899 (1995).
Korba, et al., "A Cell Culture Assay for Compounds Which Inhibit Hepatitis B Virus Replication," *Antiviral Res.*, 217:217 (1991).
Lieberman, et al., *Principles of Drug Development in Transplantation and Autoimmunity*, R. G. Landes Company, Austin (1996).
McManus, "Microtiter Assay for Interferon: Microspectrophotometric Quantitation of Cytopathic Effect," *Appl. Environment Microbid.*, 31:35-38 (1978).
Remington, *Pharma Sciences*, 18th ed., Mack Publication Co., Easton, PA 18042, 1435-1712 (1990) (Not Submitted).
Roizman, Bernard, *The Human Herpesvirus*, Chapter 1, 1-9 (1993).
Silva, et al., "Leflunomide and Malononitrilamides," *Am. J. Med. Sci.*, 313(5):289-301 (1997).
Stecher, et al., "Disease Modifying Anti-Rheumatic Drugs," *Ann. Report Med. Chem.*, 18:171-179 (1983).
Yura, et al., "Effects of Protein Tyrosine Kinase Inhibitors on the Replication of Herpes Simplex Virus and the Phosphorylation of Viral Proteins," Intervirology, 40:7-14, (1997).
Yura, et al., "Inhibitory Effect of Tyrphostin on the Replication of Herpes Simplex Virus Type 1," *Arch. Virol.* 140:1181-1194 (1995).
Yura, et al., "Inhibition of Herpes Simplex Virus Replication by Genistein, an Inhibitor of Protein-Tyrosine Kinase," *Arch. Virol.* 132:451-461 (1993).
Antoniadis, et al., "Comparison between mycophenolate mofetil and azathioprine based immunosuppression in pediatric renal transplantation from living related donors," *Transplantation Proceedings*, 30: 4085-4086 (1998).
Busuttil, et al., "Liver transplantation today" *Ann Intern Med* 104: 377-389 (1986).
Cailhier, et al., "CMV in kidney transplants in the Tacrolimus-Mycophenolate Era," *Transplantation Proceedings*, 33: 1196-1197 (2001).
Chapius, et al., "Effects of mycophenolic acid on human immunodeficiency virus infection in vitro and in vivo," *Nature Medicine*, 6:762-768 (2000).

Cory, et al., "Use of an aqueous soluble tetrazolium/formazan assay for cell growth assays in culture," *Cancer Communications*, 3: 207-212 (1991).
Dummer, et al., "Early infections in kidney, heart, and liver transplant recipients on cyclosporine," *Transplantation* 36: 259-267 (1983).
Dummer, et al., "Morbidity of cytomegalovirus infection in recipients of heart or heart-lung transplants who received cyclosporine" *J Infec Dis* 152: 1182-1191 (1985).
Hadley, et al., ajor infectious complications after orthotopic liver transplantation and comparison of outcomes in patients receiving cyclosporine or FK506 as primary immunosuppression *Transplantation* 59: 851-859 (1995).
Hiraoka, et al., "The effects of FK-506, a novel and potent immunosuppressant, upon murine Coxsackievirus B3 myocarditus" *J. Pharmacol Exp Ther* 260: 1386-1391 (1992).
Jain, et al., "A prospective randomized trial of Tacrolimus and prednisone versus tacrolimus, prednisone, and mycophenolate mofetil in primary adult liver transplant recipients," *Transplantation*, 66: 1395-1398 (1998).
Kim, et al., "Studies on the antiviral mechanisms of protein kinase inhibitors K-252a and KT5926 against the replication of vesicular stomatitis virus," *Biol Pharm Bull* May 1998;21(5):498-505 (1998).
Knight, et al., "Inhibition of herpes simplex virus type 1 by the experimental immunosuppressive agent leflunomide," *Transplantation*, 71: 170-174 (2001).
Lucien, et al., "Blood distribution and single-dose pharmacokinetics of leflunomide," *Therapeutic Drug Monitoring*, 17: 454-459 (1995).
Meulen, et al., "The influence of mycophenolate mofetil on the incidence and severity of primary cytomegalovirus infections and disease after renal transplantation," *Nephrology Dialysis Transplantation*, 15: 711-714 (2000).
Moreso, et al., "Incidence of leucopenia and cytomegalovirus disease in kidney transplants treated with mycophenolate mofetil combined with low cyclosporine and steroid doses," *Clinical Transplantation*, 12 (3): 198-205 (Jun. 1998).
Neyts, et al., "The novel immunosuppressive agent mycophenolate mofetil markedly potentiates the antiherpesvirus activities of acyclovir, ganciclovir, and penciclovir in vitro and in vivo," *Antimocrobial Agents and Chemotherapy*, 42: 216-222 (1998).
O'Connell, et al., "The effects of cyclosporine on acute murine Coxsackie B3 myocarditis" *Circulation* 73: 353-359 (1986).
Palmer, et al., Results of a randomized, prospective, multicenter trial of mycophenolate mofetil versus azathioprine in the prevention of acute lung allograft rejection, *Transplantation*, 71: 1772-1776 (2001).
Paterson, et al., "Infectious complications occurring in liver transplant recipients receiving mycophenolate mofetil," *Transplantation* 66: 593-598 (1998).
Sarmiento, et al., "Mycophenolate mofetil increases cytomegalovirus invasive organ disease in renal transplant patients," *Clinical Transplantation*, 14: 136-138 (2000).
Schiltknecht, et al., "In vivo effects of cyclosporine on influenze A virus-infected mice" *Cell Immunol*. 91: 227-239 (1985).
Singh, et al., "Infectious complications in liver transplant recipients on tacrolimus. Prospective analysis of 88 consecutive liver transplants." *Transplantation* 58: 774-778 (1994).
Waldman, et al., "Bidirectional transmission of infectious cytomegalovirus between monocytes and vascular endothelial cells: an in vitro model," *The Journal of Infectious Diseases*, 171: 263-272 (1995).
Waldman, et al., "Preservation of natural endothelial cytopathogenicity of cytomegalovirus by propagation in endothelial cells," *Archives of Virology*, 117: 143-164 (1991).
Watkins, et al., "Inhibition of virus-encoded thymidine kinase suppresses herpes simplex virus replication in vitro and in vivo," *Antivir. Chem Chemother* Jan. 1998; 9(1):9-18 (1998).
Xu, et al., "Synthesis, properties, and pharmacokinetic studies of N2-phenylguanine derivatives as inhibitors of herpes simplex virus thymidine kinases," *J. Med Chem* Jan. 6, 1995; 38(1):49-57 (1995).
Acs, et al., "Hepatitis B Virus Produced by Transfected Hep G2 Cells Causes Hepatitis in Chimpanzees," *Proc. Nat'l Acad. Sci.*, 84:4641 (1987).

Barnard, et al., "Acyclic Phosphonomethylether Nucleoside Inhibitors of Respiratory Viruses," *Antiviral Chem. Chemother.*, 8:223-233 (1997).

Bruggeman, et al., "Infection of Laboratory Rats with a New Cytomegalo-Like Virus," *Arch. Virol.*, 76:189 (1983).

Esther, et al., "Inhibition of Moloney Murine Leukemia Virus Replication by Tyrphostins, Tyrosine Kinase Inhibitors," FEBS Lett 341:99-103 (1994).

Fleckenstein, et al., "Cloning of the Complete Human Cytomegalovirus Genome in Cosmids," *Gene.*, 18:39 (1982).

Frenkel, et al. "HHV-6 and HHV-7 as Exogenous Agents in Human Lymphocytes," *Dev. Biol. Stand.*, 76:259-265 (1992).

Gillison, et al., "Human Herpesvirus-8," *Curr. Opin. Oncol.*, 9:440-449 (1997).

Huffman, et al., "Influenza Virus-Inhibitory Effects of a Series of Germanium- and Silicon-centered Polyaxometalates," *Antiviral Chem. Chemother.*, 8:75-83 (1997).

Isselbacher, et al., *Harrison's Principles of Internal Medicine*, 13 Ed., McGraw Hill, New York. 775-782 (1994). (Entire reference not submitted, Chapter 142 included).

Roizman, Bernard, *The Human Herpesviruses*, Chapter 1, 1-9 (1993).

Ashour et al., 5-(m-Benzyloxybenzyl) barbituric Acid Acyclonucleoside, a Uridine Phosphorylase Inhibitor, and 2',3',5'-Tri-O-Acetyluridine, a Prodrug of Uridine, as Modulators of Plasma Uridine Concentration. Biochemical Pharmacology, vol. 15, pp. 1601-1611 (1996).

Hidalgo et al., Phase I and Pharmacologic Study of PN401 and Fluorouracil in Patients with Advanced Solid Malignancies, Journal of Clinical Oncology, vol. 18, No. 1 pp. 167-177 (2000).

Kelsen et al., Phase I Trial and PN401, an Oral Prodrug of Uridine, to Prevent Toxicity from Fluorouracil in Patients with Advanced Cancer, Journal of Clinical Oncology, vol. 15, No. 4 pp. 1511-1517 (1997).

Van Groeningen et al., Reversal of 5-fluorouracil-induced toxicity by oral administration of uridine, Annals of Oncology 4:317-320 (1993).

Van Groeningen et al., Clinical and Pharmacologic Study of Orally Administered Uridine, Journal of the National Cancer Institute, vol. 83, No. 6, pp. 437-441 (1991).

The Merck Index Eleventh Edition, Merck & Co., NJ (1989), pp. 437, 1480, 1554.

Hawley's Condensed Chemical Dictionary Thirteenth Edition, Van Nostrand Reinhold, New York, NY (1997), pp. 329, 1105, 1159.

\* cited by examiner

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 1
gaggctattg tagcctacac tttgg                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 2
cagcaccatc ctcctcttcc tctgg                                          25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
caccaagtac ccctatcgcg t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

```
<400> SEQUENCE: 4
ttgtacgagt tgaattcgcg c                                            21
```

ANTI-VIRAL USES OF LEFLUNOMIDE PRODUCTS

This application claims priority of U.S. provisional application No. 60/077,552 filed Mar. 11, 1998.

BACKGROUND OF THE INVENTION

The present invention relates generally to novel anti-viral materials and methods involving leflunomide products.

Leflunomide (HWA-486) is an isoxazole derivative with a chemical name of N-(4-trifluoromethylphenyl)-5-methyl-isoxazol-4-carboxamide. After administration, the compound is rapidly converted to its active open-ring form, N-(4-trifluoromethylphenyl)-2-cyano-3-hydroxycrotonamide (A771726), which then rapidly undergoes keto-enol tautomerism to form N-(4-trifluoromethylphenyl)-2-cyano-3-oxo-butyramide, shown below.

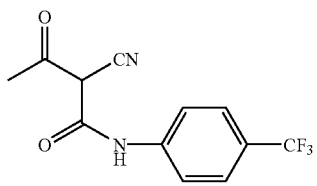

[Stecher et al., *Ann. Report Med Chem.*, 18:171-179 (1983).] Leflunomide originated from a series of compounds that were designed as agricultural herbicides by scientists at Hoechst AG. It was later found to have anti-inflammatory and immunosuppressive activity, and it has been evaluated in animal models of autoimmune disease and transplant rejection. The metabolite exhibits two mechanisms of action: inhibition of protein tyrosine kinase activity, and inhibition of dihydroorotate dehydrogenase, a key enzyme in the biosynthesis of pyrimidine nucleotide triphosphates. See generally Silva et al., *Am. J. Med. Sci.*, 313(5):289-301 (1997) and *Principles of Drug Development in Transplantation and Autoimmunity*, Lieberman and Mukherjee, eds., R. G. Landes Co., Austin (1996). The drug is well tolerated in animals and man and is currently under clinical investigation in human patients with advanced rheumatoid arthritis. No anti-viral activity has previously been reported for leflunomide or its metabolite.

U.S. Pat. No. 4,087,535 by Heubach describes a group of 5-methyl-isoxazole-4-carboxylic acid anilides having anti-inflammatory and analgesic activity. U.S. Pat. No. 4,351,841 by Kammerer et al. reports that the particular anilide designated leflunomide displays superior anti-inflammatory activity and decreased toxicity. In U.S. Pat. No. 4,351,841, leflunomide was shown to inhibit immunopathological processes in two rat adjuvant arthritis models and a rat allergic encephalitis model. U.S. Pat. No. 4,965,276 by Bartlett et al. describes the use of leflunomide to treat chronic graft vs. host (cGvH) disease and other autoimmune diseases such as systemic lupus erythematosus (SLE).

The human herpes viruses are a family of related viruses which includes herpes simplex virus 1 (HSV-1), HSV-2, varicella zoster virus (VZV), Epstein-Barr virus (EBV), cytomegalovirus (CMV), human herpesvirus 6 (HHV-6), HHV-7 and HHV-8 (also known as Kaposi's sarcoma herpesvirus, or KSHV). The herpes viruses share a similar morphology, almost indistinguishable on electron microscopy, and have a similar developmental cycle and a common ability to establish lifelong latency/persistence in the infected host. A typical herpesvirion consists of a core containing a linear double-stranded DNA, an icosadeltahedral protein capsid approximately 100 to 110 nm in diameter containing 162 capsomeres, an amorphous material surrounding the capsid designated as the tegument, and an outer lipid-containing envelope with viral glycoprotein spikes on the surface.

The members of the family Herpesviridae have been classified into three subfamilies, the Alphaherpesvirinae, Betaherpesvirinae and the Gammaherpesvirinae, on the basis of biologic properties. The Alphaherpesvirinae (including HSV-1, HSV-2 and VZV) have a variable host range, relatively short reproductive cycle, rapid spread in culture, efficient destruction of infected cells and capacity to establish latent infections primarily in the sensory ganglia. The Betaherpesvirinae (including CMV) have a restricted host range, a long reproductive cycle, a slow progression of infection in culture, frequent enlargement (cytomegalia) of infected cells, and capacity to maintain latency in secretory glands, lymphoreticular cells, kidneys and other tissue. The Gammaherpesvirinae (including EBV) have a limited host range, are specific for either T or B lymphocytes, frequently infect at a prelytic or lytic stage without production of infectious progeny, and frequently maintain latency in lymphoid tissue. See generally Chapter 1, *The Human Herpesviruses*, Roizman et al. eds., Raven Press, New York (1993); *Harrison's Principles of Internal Medicine*, 13th ed., Isselbacher et al., eds., McGraw-Hill, NY (1994); Frenkel et al., *Dev. Biol. Stand*, 76;259-265 (1992); Gillison et al., *Curr. Opin. Oncol.*, 9:440-449 (1997).

In some cases, infection of cells with herpes virus does not result in cell death. Instead, the viral genome is maintained by the cell in a repressed state compatible with survival and normal activities of the cell, a process called latency. Subsequently, activation of the viral genome may occur, resulting in viral replication and reactivation of pathogenic disease, particularly in immunocompromised patients.

HSV infections are found worldwide. Over 90 percent of adults have antibodies to HSV-1 by the fifth decade. In lower socioeconomic populations, most persons will acquire HSV-1 infection before the third decade. The clinical manifestations and course of HSV depend on the site of the infection, the age and immune status of the host, and type of virus. HSV can infect nearly all visceral or mucocutaneous sites and cause, e.g., pharyngitis or gingivostomatitis; ophthalmitis (the most frequent cause of corneal blindness in the United States); encephalitis (causing 10 to 20 percent of all encephalitis cases) or central nervous system (CNS) involvement; infection of visceral organs such as the esophagus, lung or liver, usually resulting from viremia; and other complications including monoarticular arthritis, adrenal necrosis, idiopathic thrombocytopenia and glomerulonephritis. Neonates (<6 weeks of age) have the highest frequency of visceral and/or CNS infection of any HSV-infected patient population. Without therapy, the overall mortality of neonatal herpes is 65 percent, and less than 10 percent of neonates with CNS infection experience normal development. Antiviral chemotherapy has reduced the mortality of neonatal herpes to 25 percent, but morbidity is still very high, especially in infants with HSV-2 CNS involvement.

HSV can be diagnosed by histological examination of samples from the lesions. Staining with Wright, Giemsa (Tzanck preparation), or Papanicolaou's stain will show characteristic giant cells or intranuclear inclusions typical of a herpesvirus infection. Confirmation of HSV infection is best performed by isolation of virus in tissue culture or demonstration of HSV antigens or DNA in lesions. For mucocutaneous infections, acyclovir has been the mainstay of therapy. Idoxuridine, trifluorothymidine, and vidarabine are available for topical use in HSV eye infections. For HSV encephalitis, intravenous acyclovir is the treatment of choice. For neonatal HSV infections, high-dose intravenous vidarabine and acyclovir are effective.

VZV causes two distinct clinical entities: varicella, also known as chickenpox, and herpes zoster, also known as shingles. It is most likely transmitted by the respiratory route, followed by localized replication at an undefined site, presumably the nasopharynx, leading to seeding of the reticuloendothelial system with, ultimately, viremia. The characteristic skin lesions of chickenpox are its most prominent manifestation. Chickenpox is highly contagious, with an attack rate of at least 90 percent among susceptible or seronegative individuals. Children between the ages of 5 and 9 account for 50 percent of all cases. Immunocompromised individuals have more numerous lesions which take longer to heal, and are at greater risk for visceral complications, which occur in 30 to 50 percent of cases and which are fatal in 15 percent. Neonatal varicella infection is associated with a mortality rate as high as 30 percent. Other complications of VZV infection include CNS involvement; varicella pneumonia; myocarditis; corneal lesions; nephritis; arthritis; bleeding diatheses; acute glomerulonephritis and hepatitis. Some hepatic involvement is common in chickenpox and is usually asymptomatic.

The mechanism of reactivation of VZV that results in herpes zoster is unknown. It is presumed that virus infects the dorsal root ganglia during chickenpox, where it remains latent until reactivated. The reactivation in the immunocompromised host is more severe than in the normal individual. Among patients with cutaneous dissemination, there is a 5 to 10 percent increased risk of pneumonitis, meningoencephalitis, hepatitis, and other serious complications. However, even in immunocompromised patients, disseminated zoster is rarely fatal. Patients who have had a bone marrow transplant are at particular risk of VZV infection; 45 percent of such patients have cutaneous or visceral dissemination, and the overall mortality rate is 10 percent.

VZV infection is typically diagnosed clinically from the characteristic rash of chickenpox. Unequivocal confirmation of the diagnosis is possible through the isolation of virus in susceptible tissue culture cell lines or by the demonstration of seroconversion or a fourfold or greater antibody rise in convalescent versus acute specimens. Immune prophylaxis can be accomplished by the administration of appropriate immune globulin. Both chickenpox and herpes zoster in the immunocompromised host should be treated with intravenous vidarabine or, preferably, intravenous acyclovir (preferred because of decreased toxicity) at a dose of 10 to 12.5 mg/kg every 8 hours for 7 days.

EBV has a worldwide distribution and is transmitted primarily in saliva or, less commonly, by blood transfusion. In industrialized countries, approximately 50 percent of individuals have experienced a primary EBV infection by adolescence; by adulthood, most individuals are EBV-seropositive. Primary infection with EBV during childhood is usually subclinical, but most adolescents and adults develop the clinical syndrome of infectious mononucleosis, in which symptoms of malaise, anorexia, and chills precede the onset of pharyngitis, fever, and lymphadenopathy by several days. About half of all patients develop splenomegaly. Other complications of EBV infection include hepatitis; hematologic complications such as autoimmune hemolytic anemia, mild thrombocytopenia, and granulocytopenia; neurologic complications such as cranial nerve palsies and encephalitis; and rare cardiac complications such as pericarditis and myocarditis. The condition known as X-linked lymphoproliferative (XLP) or Duncan's syndrome results in the death of 40 percent of affected males during primary EBV infection. EBV infection is also associated with certain carcinomas and lymphomas, including African Burkitt's lymphoma, anaplastic nasopharyngeal carcinoma, lymphocytic lymphoma and B cell malignancies, particularly in immunosuppressed individuals.

EBV reactivation in immunosuppressed individuals, like CMV reactivation, is frequently associated with a return of the immunoregulatory abnormalities characteristic of the primary immune response to these viruses. The cellular hyporesponsiveness associated with EBV reactivation is generally less intense and less prolonged than that associated with CMV but may contribute to morbidity in immunocompromised individuals.

Primary EBV infection may be diagnosed clinically upon signs and symptoms of infectious mononucleosis, including a relative and absolute lymphocytosis with atypical morphology. The presence of heterophil antibodies can help in diagnosis, but more specific and sensitive tests use EBV-specific antibodies. Isolating EBV in culture is not diagnostic of primary infection because of the ubiquity of the virus among EBV-seropositive individuals. Generally, supportive therapy is sufficient for EBV infection. Acyclovir, α-interferon, and ganciclovir are active inhibitors of EBV replication in vitro.

Although less is known of the more recently discovered HHV-6 and HHV-7 (both of which appear to be primarily lymphotropic), epidemiologic studies indicate that, like other members of the herpesvirus family, both are widespread among normal healthy adults, and that both may contribute to a variety of disease procedsses in the immunocompromised patient. HHV-8, the most recently discovered human herpesvirus, has been implicated as a causative agent, or important contributing factor, in the development of Kaposi's sarcoma, Castleman's disease and primary effusion lymphomas.

Cytomegalovirus (CMV) has a worldwide distribution and is an important pathogen in all age groups. In addition to inducing severe birth defects, CMV causes a wide spectrum of disorders in older children and adults, ranging from an asymptomatic, subclinical infection, to a mononucleosis-like syndrome, to disseminated disease in the immunocompromised patient. The disease name originated in the observation of characteristic cytomegalic cells, which are presumed to be infected epithelial cells. They are two to four times larger than surrounding cells and often contain an 8- to 10-μm intranuclear inclusion that is eccentrically placed and surrounded by a clear halo, resulting in an "owl's eye" appearance.

Approximately 1 percent of newborns in the United States are infected with CMV, and the percentage is higher in many less-developed countries. Cytomegalic inclusion disease develops in approximately 5 percent of congenital fetal CMV infections, and is characterized by petechiae, hepatosplenomegaly and jaundice in 60-80% of patients, and microcephaly, intrauterine growth retardation, and prematurity in 30-50% of patients. Even asymptomatic infants may develop significant psychomotor, hearing, ocular, or dental abnormalities. Neonatal infection is usually asymptomatic but may result in interstitial pneumonitis, adenopathy, rash, hepatitis, anemia, and atypical lymphocytosis.

CMV infection in healthy children and adults is typically subclinical, but may manifest as a heterophil-antibody-negative mononucleosis-like syndrome, including an atypical lymphocytosis. In CMV mononucleosis, however, exudative pharyngitis and cervical lymphadenopathy are rare. Once infected, an individual probably carries the virus for life. Most commonly, the infection remains latent. However, reactivation can occur when T-lymphocyte-mediated immunity is compromised, for example, after organ transplantation or in association with lymphoid neoplasms and certain acquired immunodeficiencies. CMV may itself contribute to further T-lymphocyte hyporesponsiveness, which often precedes superinfection with other opportunistic pathogens, such as *Pneumocystis carinii.*

CMV infection is serious only in the immunocompromised host. CMV has become recognized as an important pathogen in patients with AIDS. CMV infection is nearly ubiquitous in patients with AIDS and often causes retinitis; hepatitis; respiratory and gastrointestinal involvement; and disseminated disease. Fatal CMV infections are often associated with persistent viremia and multiple organ system involvement.

CMV also appears to be the most frequent and important viral pathogen complicating organ transplantation. Most primary CMV infections in organ transplant recipients result from transmission of the virus in the graft itself or from blood transfusion. In renal, cardiac, lung, and liver transplant recipients, CMV induces a variety of syndromes, including fever and leukopenia, hepatitis, pneumonitis, esophagitis, gastritis, colitis, and retinitis. The maximal period of risk is between 1 and 4 months after transplantation, although retinitis may be a later complication. Even transplant recipients that are seropositive from a previous infection are still susceptible to re-infection with a variant donor-derived CMV. Reactivation infection, although frequent, is generally less severe. CMV pneumonia occurs in nearly 15 to 20 percent of bone marrow transplant recipients, with a mortality rate of 84 to 88 percent. In addition, CMV infection has been implicated as a contributing factor in allograft rejection.

CMV is preferably diagnosed by isolation of virus from appropriate clinical specimens by culturing on human fibroblast monolayers. Detection of CMV viremia is a good predictor of acute infection. CMV may also be diagnosed by detecting CMV immediate-early antigens or CMV DNA in peripheral blood leukocytes. CMV immune globulin has been reported to reduce CMV-associated syndromes and superinfections some patient populations. CMV infections are usually treated with ganciclovir, which has considerably more activity against CMV than its congener acyclovir, or foscarnet. The usual dosage for CMV retinitis is 5 mg/kg IV ganciclovir twice daily for 14 to 21 days followed by 5 mg/kg daily for 5 to 7 days per week. The usual regimen of foscarnet for CMV retinitis is induction with 60 mg/kg IV every 8 h for 14 to 21 days, followed by daily maintenance infusions of 90 to 120 mg/kg.

Viral replication has both nuclear and cytoplasmic phases. The initial steps of replication include attachment of the virus to the host cell and fusion to the host cell membrane, to liberate the nucleocapsid into the cytoplasm of the cell, followed by disassembly of the nucleocapid to release and viral DNA. The virus first initiates transcription of a set of viral genes termed α-genes (also known as the "immediate early" group). The presence of the α-gene products is required for synthesis of the subsequent polypeptide group, the β-polypeptides, many of which are regulatory proteins and enzymes required for DNA replication. Most current antiviral drugs interrupt β proteins such as the viral DNA polymerase enzyme. The third (γ) class of viral genes products constitute most of the structural proteins of the virus.

Following replication of the viral genome and synthesis of structural proteins, nucleocapsids are assembled in the nucleus of the host cell. Although many details remain to be resolved regarding acquisition of the tegument and envelope, as well as virion transport to the cell surface, some studies have suggested that envelopment occurs as the nucleocapids bud through the inner nuclear membrane into the perinuclear space. Virions then may be transported via the endoplasmic reticulum and the Golgi apparatus to the cell surface.

Most of the anti-viral agents available act by inhibiting viral DNA replication. See generally Chapter 142, "Antiviral Chemotherapy," *Harrison's Principles of internal Medicine,* 13th ed., Isselbacher et al., eds., McGraw-Hill, NY (1994). Ganciclovir, 9-[(1,3-dihydroxy-2-propoxy) methyl] guanine, is a nucleoside analogue of guanosine. The triphosphate form is incorporated into replicating viral DNA, where its presence dramatically impedes chain elongation by the viral DNA polymerase. It has activity against all herpes viruses but markedly increased activity against CMV. It is available only for intravenous administration and is most commonly administered at an initial therapeutic dose of 5 mg/kg twice a day for 14 to 21 days, followed by a maintenance dose of 5 mg/kg per day or 5 times per week, possibly for as long as the immunosuppression persists. Administration of ganciclovir has been associated with profound bone marrow suppression, particularly neutropenia, which represents a major limitation of its use in many patients. Bone marrow toxicity is potentiated when other bone marrow suppressants such as zidovudine are used concomitantly.

Foscarnet (sodium phosphonoformate, or PFA) is a pyrophosphate-containing compound which is a potent inhibitor of herpes viruses, including CMV. It inhibits viral DNA replication by binding directly to the viral DNA polymerase. Foscarnet is poorly soluble and must be administered intravenously in a dilute solution infused over 1 to 2 h. The most common initial dosage of foscarnet is 60 mg/kg every 8 h for 14 to 21 days, followed by a maintenance dose of 90 to 120 mg/kg given once a day. Foscarnet exhibits considerable toxicity, including renal dysfunction, hypomagnesemia, hypokalemia, hypocalcemia, seizures, fever, and rash, each occurring in more than 5 percent of recipients. Although hematologic abnormalities also have been observed, foscarnet is not generally myelosuppressive.

Cidofovir, recently approved for use in CMV retinitis, is a monophosphorylated nucleoside analogue which, similar to ganciclovir, is further phosphorylated by cellular kinases, ultimately impeding viral DNA synthesis following incorporation into nascent strands. However, the documented nephrotoxicity of this agent necessitates careful patient selection, as well as concomitant intravenous and oral hydration and probenecid administration. Neutropenia also has been observed in approximately 10% of recipients.

Acyclovir (9-[(2-hydroxyethoxy)methyl]guanine) is an acyclic analogue of guanosine. The triphosphate form binds viral DNA polymerase and acts as a DNA chain terminator. It is relatively ineffective in CMV infections. The major adverse effect is alteration of renal function. High doses can cause an elevation of serum creatinine in as many as 50% of recipients and can occasionally cause acute renal dysfunction. There have also been reports of some central nervous system toxicity after intravenous administration.

Vidarabidine (9-β-D-arabinofuranosyladenine) is a purine nucleoside analogue that inhibits viral DNA synthesis through its triphosphate form. At higher doses, the drug has been associated with hematopoietic side effects, including anemia, leukopenia and thrombocytopenia. Neurotoxicity has also been reported.

Rhinoviruses are the major known causative agents of adult upper respiratory illnesses such as common colds. They are isolated from about 15 to 40 percent of adults with these illnesses. Only 4 to 5 percent of children with upper respiratory tract illnesses are rhinovirus positive. Rhinoviruses are a subgroup of the picornavirus family and possess certain common characteristics, including small size (15 to 30 nm), an RNA core, ether resistance and complete or almost complete inactivation at pH 3 (in contrast to the enteroviruses, which are stable at pH 3). There are over 100 different rhinovirus serotypes. In general, viral rhinitis is accompanied by thickening, hyperemia and edema of the nasal mucosa, with secretory hyperactivity of the mucus-secreting glands.

Measles is an acute, highly contagious viral disease characterized by fever, coryza, cough, conjunctivitis, enanthen and exanthem. Its morbidity and mortality vary greatly with host and environmental factors. Measles virus is an enveloped RNA paramyxovirus measuring 120 to 250 nm in diameter, similar to other members of the paramyxovirus family (genus morbillivirus) but lacking a neuraminidase. Its single antigenic serotype has been very stable worldwide for many years. The virus contains six major polypeptides which are responsible for a number of structural and functional properties, including hemagglutination of erythrocytes, hemolysis, cell fusion, viral assembly and virus penetration. Clinically, after an incubation period of about 11 days, symptoms of fever, malaise, myalgia and headache are observed, followed closely by ocular symptoms of photophobia and burning pain, inflammation of the respiratory tract and sometimes lesions of the palate, pharynx or buccal mucosa. The characteristic measles rash follows these prodromal symptoms by 2-4 days and appears on the face and neck, spreading downwards over the trunk and eventually to the extremities. Although uncomplicated measles is rarely fatal, a rare (0.1%) but serious consequence of measles is an encephalomyelitis that may result in death in about 10% of patients and permanent effects in about half of patients.

Acute viral hepatitis can be caused by a number of viral agents that have a relative or absolute predilection for the hepatocyte. The spectrum of hepatitis infection ranges from subclinical infection to rapidly progressive and fatal disease. After a variable incubation period, viral replication in the liver cell approaches maximum, followed by appearance of viral components in body fluids, liver cell necrosis and associated changes in laboratory tests of liver function and clinical signs of liver damage. Hepatitis A is an RNA enterovirus. Hepatitis B virus (HBV) is a quite different virus which causes a wide variety of acute and chronic hepatic and extrahepatic diseases. HBV is a 42 nm DNA virus with antigenically distinct surface and core components. About 90% of patients infected with HBV recover completely; of the remaining 10%, fewer than 1% develop massive hepatic necrosis, but a significant number may develop chronic hepatitis. Famciclovir has been shown to inhibit HBV replication and is being studied for treatment of chronic hepatitis B. Additional hepatitis viruses have been discovered, including hepatitis C, D and E.

There remains a need for additional anti-viral agents, which preferably have a mechanism of action that differs from currently known anti-viral agents, and which ideally exhibit superior effects when combined with other anti-viral agents.

SUMMARY OF THE INVENTION

The present invention provides novel anti-viral therapeutic uses for leflunomide products and is based on the discovery that leflunomide inhibits the replication of viruses. Leflunomide has been discovered to inhibit viral growth in a manner different from other conventional anti-viral agents, which typically act by inhibiting viral DNA replication in the early stages of infection. In contrast, leflunomide appears to act by inhibiting virion assembly. Thus, therapeutically effective anti-viral amounts of leflunomide product include amounts effective for inhibiting viral growth or inhibiting virion assembly. The unique mechanism of action of leflunomide products allows these drugs to be effective against viruses that are resistant to other conventional anti-viral agents, including multi-drug resistant viruses.

According to one aspect of the invention, therapeutically effective amounts of leflunomide products are administered to subjects, including mammals, suffering from viral infection, particularly infection by herpesvirus (including CMV, HSV-1, HSV-2, VZV, EBV, HHV-6, HHV-7 and HIV-8), paramyxoviruses (including parainfluenza, mumps, measles and respiratory syncytial virus), picornaviruses (including enteroviruses and rhinoviruses) and hepatitis viruses (including hepatitis A, B, C, D and E). The leflunomide product can be administered to humans in doses ranging from about 0.1 mg to 80 mg daily, varying in children and adults, or more preferably at doses ranging from about 15 mg to 25 mg daily, or in equivalent doses at longer intervals.

It is contemplated that leflunomide products may be concurrently administered with other known anti-viral agents, in which case the dosage of each agent required to exert a therapeutic effect during combinative therapy may be less than the dosage necessary for monotherapeutic effectiveness.

According to another aspect of the invention, a leflunomide product is co-administered with a pyrimidine, such as uridine, in order to reduce its toxicity while maintaining its therapeutic effectiveness. It is contemplated that co-administration with a pyrimidine may allow administration of an anti-viral therapeutically effective amount of leflunomide product with reduced immunosuppressive or toxic side effects.

Another aspect of the invention contemplates a method of inhibiting viral replication by contacting a cell that has been infected by a virus with an anti-viral amount of leflunomide product.

Veterinary anti-viral uses of leflunomide product are also contemplated.

Numerous additional aspects and advantages of the invention will become apparent to those skilled in the art upon consideration of the following detailed description of the invention which describes presently preferred embodiments thereof

DETAILED DESCRIPTION

Figure 1:
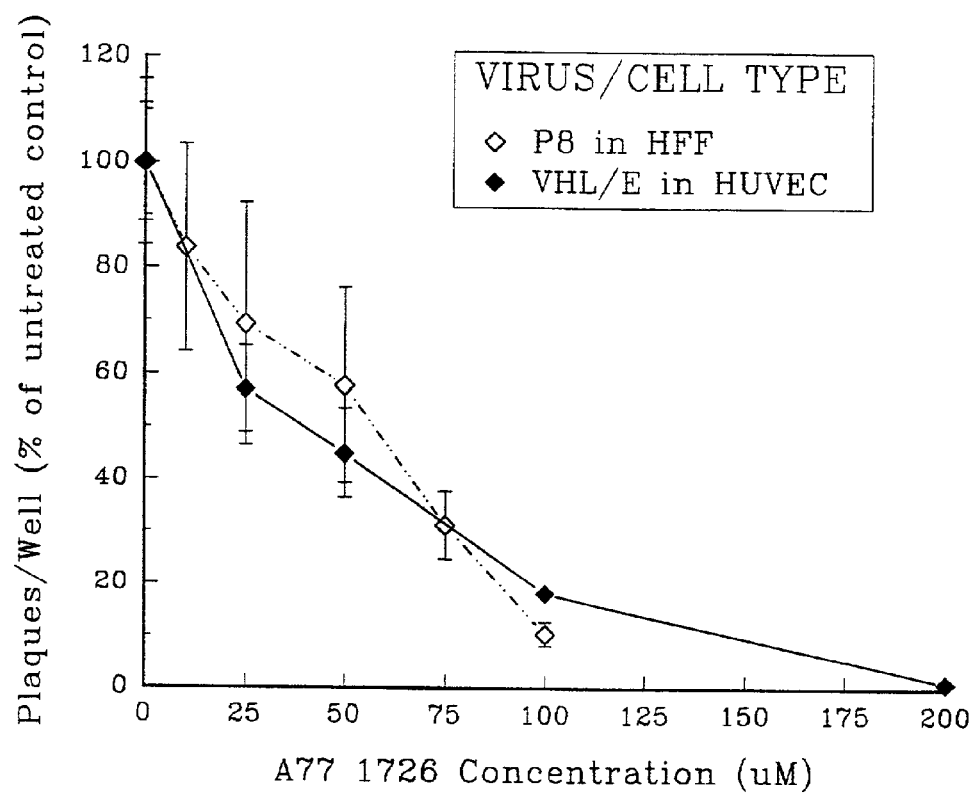
FIG. 1 displays plaque assay data demonstrating A771726-mediated attenuation of production of CMV strain P8 in human foreskin fibroblasts (HFF) and CMV strain VHL/E in human umbilical vein endothelial cells (HUVEC).

The present invention provides novel anti-viral therapeutic uses for leflunomide products and is based on the discovery described herein that in vitro, leflunomide's active metabolite N-(4-trifluoromethylphenyl)-2-cyano-3-hydroxycrotonamide (A771726) inhibits the replication of a variety of viruses, including CMV, HSV, measles virus, rhinovirus, and hepatitis B and C viruses, and that A771726 has been confirmed to inhibit viral replication in vivo. Unlike conventional anti-viral agents, this leflunomide product acts at a late stage in virion maturation and assembly by preventing tegument acquisition by viral nucleocapsids. The resulting incomplete virions are not active and therefore cannot infect other cells. Although knowledge of the structural organization of the herpes virus tegument is incomplete, many of the major tegument proteins are phosphoproteins for which kinase-mediated phosphorylation is required. Thus, leflunomide product may interfere with tegument assembly by inhibiting protein phosphorylation through its inhibition of tyrosine kinase activity.

The unique mechanism of action of leflunomide products allows these drugs to be effective against viruses that are resistant to other conventional anti-viral agents. A multi-drug resistant strain of CMV is shown herein to be as equally sensitive to leflunomide product as drug-sensitive strains of CMV.

According to one aspect of the invention, therapeutically effective amounts of a leflunomide product are administered to subjects, including mammals, suffering from viral infection. The invention contemplates treatment of infection by any virus, including herpesviruses (including CMV, HSV-1, HSV-2, VZV, EBV, HHV-6, HHV-7 and HHV-8), paramyxoviruses (including parainfluenza, mumps, measles, and respiratory syncytial virus (RSV)), picornaviruses (including enteroviruses and rhinoviruses), togaviruses, coronaviruses, arenaviruses, bunyaviruses, rhabdoviruses, orthomyxoviruses (including influenza A, B and C viruses), reoviruses (including reoviruses, rotaviruses and orbiviruses). parvoviruses, adenoviruses, hepatitis viruses (including A, B, C, D and E) and retroviruses (including HTLV and HIV). Treatment of both acute and chronic infection are contemplated.

Anti-viral therapeutically effective amounts of leflunomide product include amounts effective for inhibiting viral growth, i.e., replication, or inhibiting virion assembly. The leflunomide product can be administered to humans at doses ranging from about 0.1 to 80 mg daily, varying in children and adults, or more preferably at doses ranging from about 15 to 25 mg daily for adults. Most preferable are doses calculated to provide a circulating blood level of about 40 to 60 μM. Equivalent dosing of leflunomide product can be administered at longer intervals, e.g., larger doses once or twice weekly, due to the longer half-life of 2-5 days of leflunomide product in humans. The therapeutically effective dose may be adjusted to provide maximum reduction in viral replication or infection without resulting in excessive toxicity. The dose of leflunomide product required to produce anti-viral effects is also expected to be lower than the dose required to provide immunosuppressive effects. In animal studies, extremely high doses of leflunomide result in liver and cardiac toxicity. In humans, a side effect of accumulation of the metabolite trifluoromethyl aniline is a Heinz-body hemolytic anemia; the appearance of anemia in a patient thus may be an early, sensitive sign of adverse side effects due to leflunomide product administration and an index of adequacy of drug dosing.

Leflunomide product may be administered systemically via, e.g., oral, intravenous, intramuscular or subcutaneous routes. The drug may be aerosolized for pulmonary administration, formulated in a spray for nasal administration, administered intraventricularly or intrathecally into the cerebrospinal fluid, or administered intravenously via continuous infusion pump. The drugs may also be administered topically via, e.g., drops (particularly ophthalmic drops), ointment, patch or per rectum via e.g., suppositories or enemas. For the combination treatments, leflunomide product and another anti-viral agent can be administered simultaneously or sequentially.

This aspect of the invention therefore contemplates use of a leflunomide product in the preparation of a medicament for treating viral infection.

The invention may also be practiced by administering leflunomide product in combination with therapeutically effective amounts of one or more non-leflunomide anti-viral agents, including acyclovir, ganciclovir, vidarabidine, foscarnet, cidofovir, amantidine, ribavirin, trifluorothymidine, interferon-alpha, zidovudine, didanosine, or zalcitabine. The therapeutically effective doses of all of these drugs, including leflunomide, in the combinative therapy will be lower than the usual doses of each drug used for single drug monotherapy.

Viral infection, particularly herpes virus infection, is associated with an increased incidence of cancers. It is expected that treatment with leflunomide product may prevent or reduce the growth of these cancers. For example, EBV is associated with African Burkitt's lymphoma, anaplastic nasopharyngeal carcinoma, lymphocytic lymphoma and B cell malignancies, while HHV-8 is associated with Kaposi's sarcoma.

Another aspect of the invention contemplates a method of inhibiting viral replication by contacting a cell that has been infected by a virus with an anti-viral amount of leflunomide product. The invention contemplates inhibiting replication of any virus, including herpesviruses (including CMV, HSV-1, HSV-2, VZV, EBV, HHV-6, HHV-7 and HHV-8), paramyxoviruses (including parainfluenza, mumps, measles, and respiratory syncytial virus (RSV)), picornaviruses (including enteroviruses and rhinoviruses), togaviruses, coronaviruses, arenaviruses, bunyaviruses, rhabdoviruses, orthomyxoviruses (including influenza A, B and C viruses), reoviruses (including reoviruses, rotaviruses and orbiviruses), parvoviruses, adenoviruses, hepatitis viruses (including A, B, C, D and E) and retroviruses (including HTLV and HIV).

The term "leflunomide product" as used herein means leflunomide, N-(4-trifluoromethylphenyl)-5-methylisoxazol-4-carboxamide (HWA-486), or its active metabolite, N-(4-trifluoromethylphenyl)-2-cyano-3-hydroxycrotonamide (A771726), or other related derivatives (such as those described in U.S. Pat. Nos. 4,087,535 and 5,519,042 (formulas I and II), both of which are incorporated herein by reference) or metabolites thereof that retain all or part of the anti-viral activity of leflunomide, including products represented by the following chemical formula:

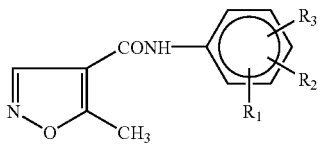

wherein (A) R1 and R2 are each hydrogen and R3 is halogen, —CF₃, alkoxy having 1 or 2 carbon atoms, or halo-substituted alkoxy having 1 or 2 carbon atoms;
(B) R1 is hydrogen and R2 and R3, which are the same or different, are halogen or —CF₃;
(C) R1 is hydrogen, R2 is alkyl having 1 or 2 carbon atoms, and R3 is halogen; or
(D) R1 is hydrogen and R2 and R3 are 3',4'-methylene dioxy;

and also including amides of malononitriles represented by the following formula:

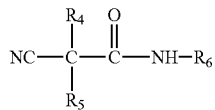

wherein R4 is H or R₇; R5 is H or COR₇; R6 is trifluoromethylphenyl or another substituted phenyl as described immediately above; and R7 is an alkyl group having 1, 2, 3 or 4 carbon atoms.

Also contemplated are a compound of formula I or II

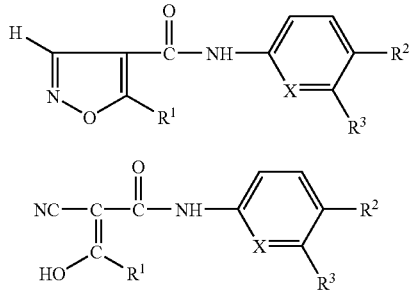

wherein
R¹ denotes
a) methyl,
b) (C₃-C₆)-cycloalkyl,
c) (C₂-C₆)-alkyl, having at least 1 triple or double bond between the carbon atoms,
R² denotes
a) —CF₃ or
b) —CN,
R³ denotes
a) (C₁-C₄)-alkyl or
b) hydrogen atom,
X denotes
a) —CH-group or
b) nitrogen atom,
the compound of the formula II being present as such or in the form of a physiologically tolerable salt.

Preferred are compounds of the formula I or II wherein
R¹ denotes
a) methyl,
b) cyclopropyl or
c) —CH₂—CH₂—C≡CH,
R² denotes —CF₃
R³ denotes methyl or hydrogen atom and
X denotes —CE— group.

Especially preferred is a compound of the formula I or II, wherein R¹ denotes methyl, R² denotes —CF₃, R³ denotes hydrogen atom and X denotes —CH-group.

Such products can be prepared by methods known in the art, including those described in U.S. Pat. Nos. 4,087,535, 4,351,841 and 4,965,276, all of which are incorporated herein by reference.

A treatment capable of inhibiting viral growth, or replication, is a treatment that arrests or inhibits the maturation of the complete virion and consequently arrests or reduces the spread of infection to other host cells.

The methods of the present invention can be used to treat patients at risk of viral infection or patients already infected with virus. Thus, "treatment" as used herein means both prophylactic and therapeutic treatment. It is contemplated that leflunomide product is particularly useful in treating patients receiving organ transplants, including skin, heart, lung, kidney, liver, pancreatic islet cells, bone marrow transplants, other allografts, combination allografts such as heart-lung, and xenografts. These patients have a high risk of developing serious viral infections, particularly CMV infections, post-transplant. CMV infection is a particularly serious disease in bone marrow transplant recipients. Because of its low toxicity and dual functionality as a graft-preserving immunosuppressant and an anti-viral agent effective even against drug-resistant viruses, leflunomide product is advantageously administered to these patients in place of or as a part of an ongoing immunosuppressive regimen.

According to another aspect of the invention, a leflunomide product is co-administered with a pyrimidine, such as uridine, in order to reduce its potential toxicity while maintaining its therapeutic effectiveness. It is contemplated that co-administration with a pyrimidine may allow administration of an anti-viral therapeutically effective amount of leflunomide product with reduced immunosuppressive or toxic side effects. Anti-viral amounts of leflunomide product may be administered to healthy immunocompetent individuals, neonates or immunocompromised patients, including patients suffering from AIDS, or patients with cancer or undergoing chemotherapy, or patients with other defects in their immune system, without causing significant further depression of their immune system.

As used herein, a "pyrimidine" includes compounds useful either directly or as intermediates in pathways for supplying pyrimidine nucleotides (uridine, cytidine and thymidine). A preferred pyrimidine is uridine. Other suitable pyrimidines include the pyrimidine intermediates orotic acid and orotidine. Other exemplary pyrimidines include cytidine and thymidine, possibly at higher doses.

Pyrimidine compositions are generally administered in doses ranging from 1 mg/kg to 5000 mg/kg per day, preferably in doses ranging from 50 mg/kg to 200 mg/kg per day given orally, or in equivalent dosing at longer or shorter intervals. Pyrimidines are generally not well absorbed orally, so other systemic routes of administration such as intravenous administration may be preferable to maintain appropriate serum levels of uridine. Humans with orotic aciduria are generally given uridine supplementation at doses of 150 mg/kg.

The dosage of leflunomide product and/or pyrimidine may be increased or decreased, and the duration of treatment may be shortened or lengthened as determined by the treating physician. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the administered agents.

Those of ordinary skill in the art will readily optimize effective dosages and concurrent administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels for the treatment of various diseases and conditions.

Yet a further aspect of the invention provides a method of screening for a leflunomide product or derivative thereof having anti-viral activity comprising the steps of (a) growing a virus in cell culture, (b) contacting the virus-infected cells with a test amount of leflunomide product or derivative thereof, and (c) determining the effect of the test amount on viral growth. Any virus can be used to test for activity, including HSV, CMV, measles virus, rhinovirus, and hepatitis B or C viruses. Also contemplated are novel leflunomide products or derivatives thereof identified by such a screening method.

The present invention thus makes possible the identification of leflunomide products, including derivatives and related compounds, that retain the same anti-viral activity of leflunomide and A771726 or possess even greater anti-viral efficacy. When such products are additionally screened for immunosuppressive activity, the identification of products with good anti-viral activity and reduced immunosuppressive activity is possible. Ideally, a compound with primarily or exclusively anti-viral activity (very little or substantially reduced immunosuppressive activity) is used for treatment of subjects, particularly those with impaired immune systems (such as AIDS patients, cancer patients undergoing chemotherapy or radiation therapy and neonates).

Other aspects and advantages of the present invention will be understood upon consideration of the following illustrative examples. Example I addresses the in vitro effect of A771726 on CMV and HSV replication. Example 2 addresses the in vitro effect of A771726 with uridine on CMV replication. Examples 3 and 4 address the effect of A771726 on CMV DNA replication. Example 5 addresses the effect of A771726 on CMV virion assembly. Example 6 addresses the effect of A771726 on a multi-drug resistant CMV strain. Example 7 addresses the anti-viral effect of leflunomide product in vivo. Example 8 addresses the effect of A771726 on HSV. Examples 9 and 10 address the effect of several leflunomide products on a variety of viruses.

EXAMPLE 1

Plaque Assay of Leflunomide Product Effect on Infectious Virus Production

To determine the impact of leflunomide upon the production of infectious CMV in fibroblasts, standard plaque assays were performed in the presence of A771726, the active metabolite of leflunomide, at a range of concentrations equivalent to those which have been shown to attenuate immune activation by various stimuli in vitro.

Human foreskin fibroblasts (HFF) were inoculated with the clinical CMV isolate P8, overlaid with medium supplemented with 0.3% agarose and 0-100 µM A771726, then incubated for 10-14 days before plaque ennumeration under low-power microscopy. The experiments were carried out as follows. Human foreskin fibroblasts (HFF, Viromed, Minneapolis Minn.) were grown in Eagles MEM (GivcoBRL, Grand Island N.Y.) supplemented with 10% fetal bovine serum (FBS). MRC 5 human fibroblast cells (American Type Culture Collection, Rockville Md.) were propagated in MEM (Gibco) supplemented with 10% fetal bovine serum (Hyclone, Logan Utah), 1% essential amino acids, 2% non-essential amino acids, and 0.5% vitamins (Sigma, St. Louis, Mo.). CMV strains P8 (ganciclovir-sensitive) and D16 (ganciclovir-resistant) were obtained from bronchial brushing of a cardiac allograft recipient and propagated in HFF cells.

To quantitate CMV production in fibroblasts, HFF in 24-well culture plates were inoculated with strain P8 or strain D16 at titers sufficient to generate 30-60 plaques/well. Inocula were absorbed for 3-4 hours, removed, and monolayers were overlaid with medium supplemented with 0.3% agarose and various concentrations of A771726 (4 wells/concentration). Cultures were incubated 10-14 days and plaques counted by low power phase contrast microscopy.

The effect of A771726 upon CMV activity in human umbilical vein endothelial cells (HUVEC) was also investigated, as was the drug's effect upon HSV activity. Since HUVEC do not tolerate agarose-supplemented medium well, a two step procedure was necessary. HUVEC were inoculated with CMV strain VHL/E or strain BUR/E (separate clinical isolates whose natural endothelial cytopathogenicity has been preserved by propagation in HUVEC) and incubated for 7-10 days in the presence of various concentrations of A771726 (0-200 µM). Cells were then harvested and disrupted by sonication. Infectious activity within the resultant lysates was quantitated by plaque assay on MRC 5 fibroblasts.

The experiments were carried out as follows. Human umbilical vein endothelial cells (HUVEC) were isolated from cord vessels as previously described and propagated in endothelial cell growth medium (ECGM), consisting of M-199

(Gibco) supplemented with 20% FBS (Hyclone), 50 μg/mL bovine brain extract [43], 12 U/mL sodium heparin (Sigma), and 20 mM HEPES buffer. All growth surfaces for HUVEC were pretreated with Human fibronectin (Upstate Biotechnology, Lake Placid N.Y.), 25 μg/mL. Purity of all endothelial isolates was verified at passage 3 by immunoperoxidase straining for von Willebrand Factor, and absence of contaminating leukocytes was verified by uniform negativity for leukocyte common antigen (CD45), B cell antigen (CD20), and monocyte-specific antigen (CD11c). CMV strain VHL/E, isolated from duodenal biopsy material from a bone marrow transplant recipient, and strain BUR/E, isolated from urine of a renal transplant patient, were propaged in HUVEC to preserve their natural endothelial cytopathogenicity.

To quantitate CMV production in endothelial cells, confluent HUVEC monolayers in 24-well culture plates were pretreated in triplicate for 1 hour with ECGM supplemented with various concentrations of A771726, tacrolimus (FK506, Fujisawa, Deerfield Ill.), cyclosporine A (CsA, Sandoz, East Hanover, N.J.), phosphonoformate (PFA [Foscarnet], Sigma), or ganciclovir (Cytovene, Syntex, Morris Plains, N.J.). Following pre-treatment, monolayers were washed with phosphate buffered saline (PBS), inoculated with CMV strain VHL/E or BURJE (0.2-2 plaque-forming unit [PFU]/ml), and centrifuged for 30 minutes at 300×g. Following centrifugation, inocula were removed and monolayers were washed twice with PBS before addition of fresh ECGM supplemented with the agents listed above. Cells were cultured in the continuous presence of these agents with medium changes at 48-hour intervals. Following 7-10 days of incubation, cells were washed twice with PBS, harvested by brief trypsin digestion (0.005% trypsin/0.01% EDTA), disrupted by sonication, and inoculated in serial dilution onto confluent MRC5 fibroblast monolayers for plaque assay as detailed elsewhere. Data were plotted as means of triplicate or quadruplicate wells +/−1 standard deviation, normalized to untreated CMV-infected controls.

Data presented in FIG. 1, representative of 3-4 replicate experiments, demonstrate an A771726-mediated dose-dependent reduction in infectious virus production in both fibroblasts (strain P8 in HFF) and endothelial cells (strain VHL/E in HUVEC). Data points represent mean plaque numbers generated within 3-4 replicate culture wells, expressed as percent of those generated in untreated CMV-infected controls. Importantly, the dose response curves do not vary significantly between the two viral strains in their respective host cell types, and indicate a common $ID_{50}$ of 40-60 μM.

To determine whether leflunomide's anti-viral properties were shared by other commonly prescribed immunosuppressive agents, similar assays were performed in the presence of cyclosporine A (CsA) or tacrolimus (FK 506) at concentrations which have been shown to attenuate immune activation by various stimuli in vitro. Thus HUVEC were inoculated with either CMV strain VHL/E or BURIE and incubated in the presence of A771726 (200 μM), CsA (100 ng/ml), or FK 506 (1 ng/ml). As positive controls for viral inhibition, each experiment included cells treated with 1 mM phosphonoformate (PFA, Foscarnet) or 10 μg/ml ganciclovir (GCV). These data again demonstrated dramatic and statistically significant A771726-mediated attenuation of CMV production (p<0.001) with no significant inhibition by FK 506. Curiously, CsA was consistently observed to significantly enhance production of infectious virus as compared to activity within untreated infected cells.

In preliminary experiments, a similar assay using HSV instead of CMV showed that A771726 produced a definite observed reduction in plaque production.

EXAMPLE 2

Anti-viral Effect of Leflunomide Product in the Presence of Exogenous Uridine

To determine whether reduction of intracellular pyrimidine nucleotide pools was responsible for the antiviral effects of leflunomide product, HUVEC were inoculated with CMV VHL/E as described above, then incubated for 4 days in the presence or absence of 200 μM A771726, 200 μM exogenous uridine, or both. Uninfected HUVEC were included in each experiment as negative controls. Cells were harvested and small aliquots of each group were sonicated and assayed for plaque formation on MRC 5 monolayers as described above. The remainder of cells were extracted in trichloroacetic acid, then in tri-n-octylamine and 1,1,2-trichloro-trifluoro-ethane. Intracellular pyrimidine nucleotide (pyNTP) levels were quantitated by HPLC.

Confluent HUVEC monolayers in 6-well culture plates were pre-treated for 1 hour fresh ECGM alone or with ECGM supplemented with 20 μM A771726, 200 μM uridine, or both (6 wells/treatment). Following pre-treatment, monolayers were inoculated with CMV strain VHL/E (1.0 PFU/cell), then incubated in the continued presence of agents for 4 days with addition of fresh medium at 48 hours. Cells were then harvested by brief trypsin digestion, washed twice in PBS, extracted on ice in 0.4 M trichloroacetic acid, then extracted with tri-n-octylamine and 1,1,2-trichloro-trifluoro-ethane according to methods described by Khym. Intracellular nucleotide triphosphate quantitation was performed by HPLC (Waters Associates, Milford, Mass.) employing a 616 pump, a 600 S gradient controller, a 717 plus autosampler, and a 996 PDA detector, using a strong anion exchange column of Partisil-10 SAX (Alltech Assoc. Inc., Deerfield, Ill.) eluted with a gradient of 10 to 500 mM potassium phosphate (pH 4.5). The four nucleotide triphosphate peaks were quantitated by integration and comparison to standardization samples. To correlate intracellular nucleotide concentrations with viral activity, samples of cells from each treatment group (reserved prior to extraction) were disrupted by sonication and assayed for plaque formation on MRC monolayers as described above.

Intracellular pyNTP levels were reduced in untreated CMV-infected HUVEC as compared to uninfected control cells, but were not further reduced in infected cells treated with A771726. The reason for this may be that the HUVEC in the assay were in a stationary, quiescent phase in which minimal intracellular NTP consumption would be expected. The addition of exogenous uridine increased pyNTP levels both in the presence and absence of A771726.

Figure 2:
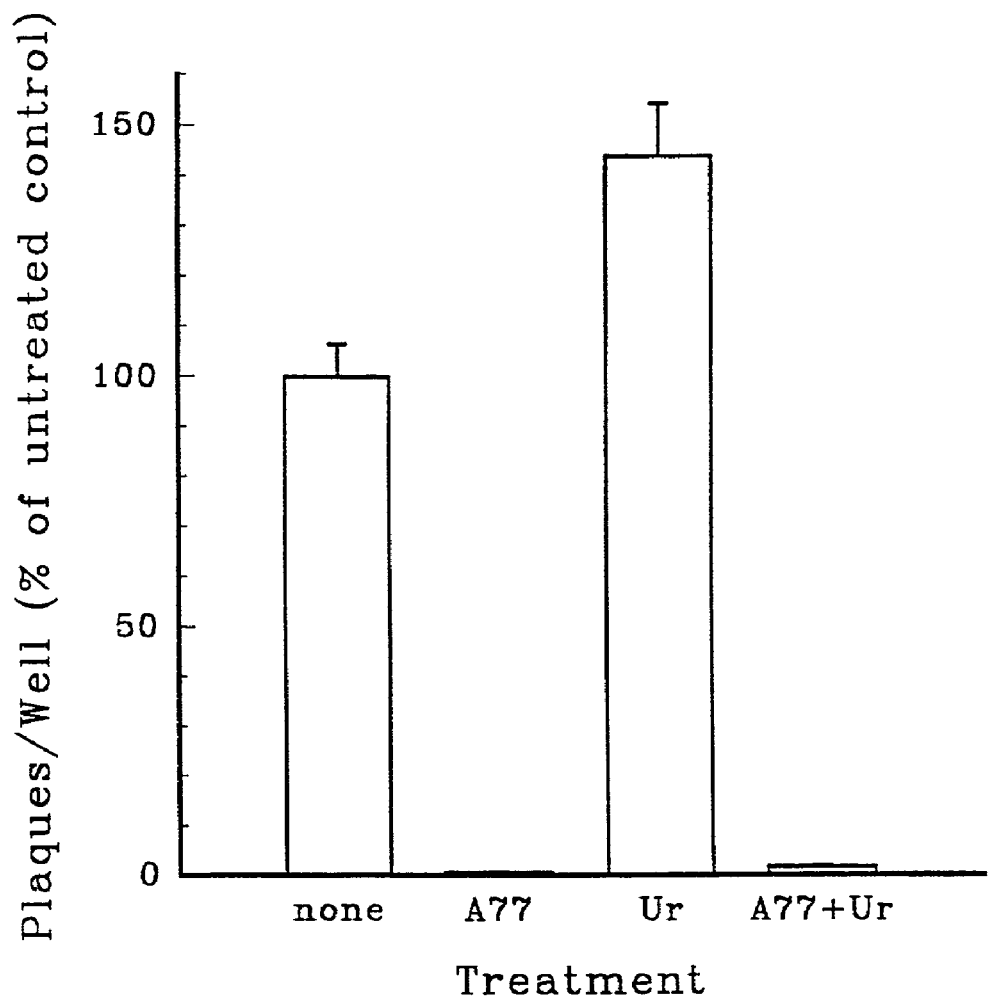
FIG. 2 displays plaque assay data of A771726-treated, CMV-infected cells with and without exogenous uridine.

More importantly, the addition of exogenous uridine did not significantly reconstitute infectious virus production in A771726-treated, CMV-infected EC (results shown in FIG. 2). Thus, A771726-mediated inhibition of CMV activity appears to be independent of the inhibitory effects of this agent upon pyNTP synthesis.

EXAMPLE 3A

Effect of Leflunomide Product on Viral Protein Expression

Experiments were conducted to determine at which point in the viral replication cycle leflunomide exerts its inhibitory effects. Immediately upon penetration of the host cell, CMV lower matrix protein pp65, a component of the viral tegument, translocates to the cell nucleus. Although the nuclear function of pp65 remains to be resolved, another tegument protein (pp71) that migrates in a similar manner acts in concert with cellular proteins to promote rapid transcription of immediate early (IE) viral genes. IE gene products are primarily regulatory, activating early gene transcription, whose products are essential for viral DNA replication. Activation of late genes, which code primarily for structural protein components of the virion, occurs late in the replicative cycle and is dependent upon viral DNA replication.

To localize potential A771726-induced lesions in this temporal series of events, a cross section of CMV proteins in infected cells was first visualized by immunohistochemical staining as follows. CMV strain VHL/E-inoculated HUVEC monolayers incubated in the presence or absence of 200 µM A771726 or 1 mM phosphonoformate (PFA) (as a positive control for late antigen inhibition) were fixed at various intervals and stained with mAb specific for pp65, 72 kD IE1, or late structural glycoproteinB (gB). Confluent HUVEC monolayers in 8-well chamber slides (Nalge Nunc International, Naperville, Ill.) were pre-treated for 1 hour with fresh ECGM alone or with ECGM supplemented with 200 µM A771726, or 1.0 mM PFA, then inoculated with CMV strain VHL/E (2 PFU/cell) as described above. Slides were incubated in the presence of absence of the agents for various intervals, acetone-fixed, and stained by the immunoperoxidase method. Primary antibodies were specific for 72 kDa CMV immediate early (IE) antigen (DuPont, Wilmington Del.), CMV lower matrix protein, pp65 (ViroStat, Portland Me.), CMV late structural glycoprotein B (gB, mAb 7-17, generously provided by Dr. William J. Britt, University of Birmingham AL), or irrelevant isotype-matched antibodies as specificity controls.

None of these viral proteins were prevented from being expressed in A771726-treated cells. At 24 hours post-inoculation (pi), nuclear accumulation of pp65 (red stain) can be seen in both untreated and A771726-treated monolayers, implying that this agent interferes with neither viral entry, nor with nuclear translocation of pp65. IE1 expression also appeared to be unaffected by A771726 (IE, 48 hr pi). Finally, typical gB staining patterns were apparent at 96 hours pi in both treated and untreated cultures. In contrast, infected cells treated with PFA, an inhibitor of CMV DNA polymerase, were unable to express gB, while pp65 and IE1 expression in these cultures was unimpeded.

The data revealed an increase in the number of infected cells in the untreated monolayers, but not in those incubated in the presence of A771726. In untreated cells, CMV strain VHL/E, in addition to retaining its natural endothelial cytopathogenicity, retained the natural tendency of CMV to remain tightly cell associated, disseminating slowly through inoculated monolayers by direct cell-to-cell transmission. It was also observed that while in untreated monolayers virus spreads to adjacent cells forming multicellular infected foci, treatment with A771726 appears to largely restrict viral activity to the individual cells infected by the primary inoculum.

Example 3B

Effect of Leflunomide Product on Viral Gene Expression

Northern blot analysis was employed to determine whether A771726 quantitatively affected transcription of viral immediate early (IE1) or late glycoprotein (gB) mRNA.

HUVEC monolayers in 6-well culture plates were inoculated with CMV strain VHL/E (0.5 PFU/cell) in the presence or absence of 200 µM A771726 and/or 200 µM uridine (6 wells/treatment) as described above, and incubated for 48 hours. Each experiment also included infected cultures treated with 1 mM PFA and 1.2 mM ganciclovir (positive control for inhibition of gB expression), as well as uninfected controls. Total cytoplasmic RNA was isolated from each culture, by 18-hour ultracentrifugation of guanidine isothiocyanate/BME extracts overlayed on cesium chloride cushions. 10 µg of total RNA from each sample was separated on a 1.4% agarose/0.22 M formaldehyde gel then transferred to a nylon membrane (Hybond-N, Amersham Corp., Arlington Heights, Ill.) and probed with labeled probes specific for IE1, gB and GAPDH (a loading control). cDNA probes for CMV IE1 and CMV gB were radiolabelled by PCR as follows. 50 ng of full-length IE1 and gB were incubated in a 50 µl PCR reaction including a nucleotide triphosphate mix containing 700 nM α-[$^{32}$P]dCTP (Amersham) and either IE1 primers [IE1 sense: 5' GAG GCT ATT GTA GCC TAC ACT TTG G 3' (SEQ ID NO: 1) and IE1 antisense: 5' CAG CAC CAT CCT CCT CTT CCT CTG G 3' (SEQ ID NO: 2)] or gB primers [gB sense: 5 CAC CAA GTA CCC CTA TCG CGT 3' (SEQ ID NO: 3) and gB antisense: 5' TTG TAC GAG TTG AAT TCG CGC 3' (SEQ ID NO: 4)]. A cDNA probe for GAPDH was radiolabelled using a random priming kit (Decaprime II, Ambion, Inc., Austin Tex. as previously described. Unincorporated isotope was removed from labeled probes using a G-50 spin column (Worthington Biochemicals, Freehold, N.J.). Membranes were hybridized, washed, and bound probe was detected by autoradiography as previously described. Membranes were stripped and reprobed for GAPDH, and scanning densitometry was used to quantitate IE1 and gB band densities, and to normalize these values to those of GAPDH.

Figure 3:
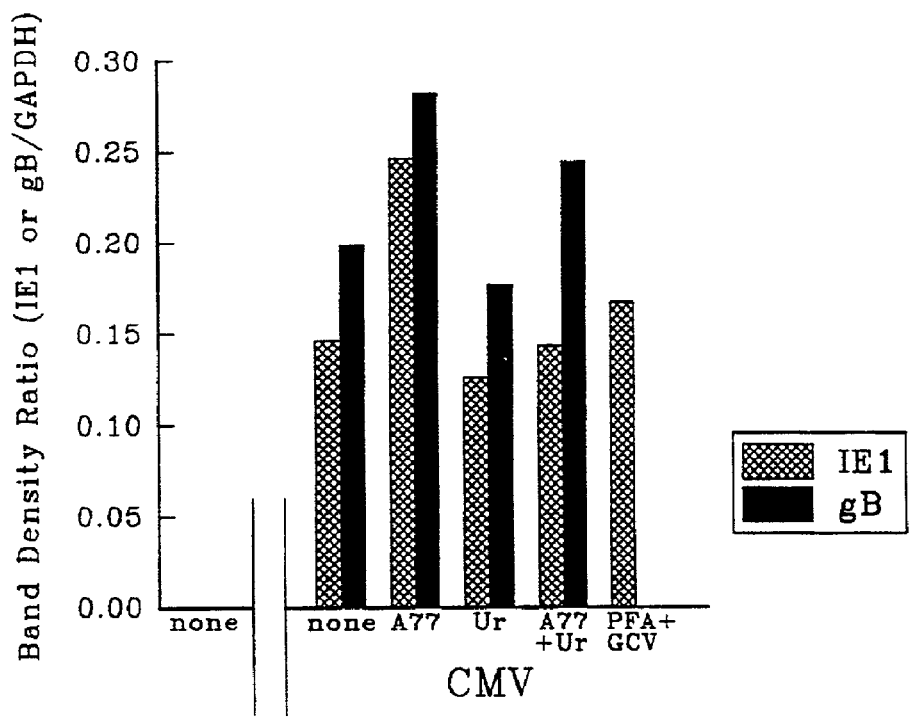
FIG. 3 displays data from Northern blot analysis of mRNA extracted from A771726-treated, CMV-infected cells showing the extent of immediate early (IE1) or late glycoprotein (gB) transcription.

Results representative of 2 replicate experiments are presented in FIG. 3. IE1 and gB band densities (as determined by scanning densitometry) are plotted as ratios to those of GAPDH. As demonstrated in this figure, while gB mRNA expression was completely suppressed in cells treated with PFA/GCV, A771726 exerts no inhibitory effect upon transcription of either IE 1 or gB genes.

EXAMPLE 4

Effect of Leflunomide Product on CMV DNA Polymerase Activity

A. Effect of Leflunomide Product on CMV DNA Synthesis

Since expression of late structural proteins (such as gB) is dependent upon CMV DNA replication, the result of Example 3 indicated that, in contrast to currently used antiviral therapeutics, leflunomide does not inhibit viral DNA synthesis. To confirm this, viral DNA was quantitated by dot blot following incubation of CMV-infected cells in the presence or absence of A771726. HUVEC or HFF monolayers in 24-well culture plates were inoculated with CMV VHL/E (1 PFU/cell) or CMV P8 (0.3 PFU/cell) respectively, and incubated in the presence or absence of 200 µM (HUVEC) or 100 µM (HFF) A771726. All experiments included infected cultures incubated in the presence of 1 mM PFA as well as uninfected controls. 48 hours post-inoculation cells were harvested by trypsin digestion, washed in PBS, and incubated for 12 hours at 50° C. in 0.1 mg/ml proteinase K (Sigma) in digestion buffer (100 mM NaCl, 10 mM Tris-HCl, 25 mM EDTA, 0.5% SDS). DNA was extracted in phenol/chloroform, precipitated with ammonium acetate/ethanol, and resuspended in TE buffer. Following equalization of concentrations, extracted DNA was serially diluted in 96-well microtiter plates and 0.4 M NaOH/10 mM EDTA was added to each well. DNA was denatured in sealed plates by heating for 10 minutes in a 100° C. waterbath, transferred to nylon membranes (Hybond N, Amersham) using a vacuum dotblot manifold (Bio-Rad Laboratories, Hercules, Calif.), and immobilized by UV cross-linking. The cDNA probe was generated by HindIII digest of cosmid pCM 1015 (Fleckenstein et al., Gene, 18:39, 1982) which contains ~45 kb of the $U_L$ region of the CMV AD169 genome. The probe was $\alpha$-[$^{32}$P]dCTP-labelled by random priming. Unincorporated isotope was removed from labelled probe using a G-50 spin column (Worthington Biochemicals). Membranes were hybridized, washed, and bound probe was detected by autoradiography.

The quantities of viral DNA synthesized in CMV-infected HFF incubated in the presence of A771726 were approximately equivalent to that accumulated in untreated infected cells. In contrast, PFA-treated cells contained no detectable CMV DNA. Identical results were observed in similarly treated HUVEC. The specificity of the probe was verified by the absence of hybridization to DNA extracted from uninfected cells.

B. Effect of Leflunomide Product on CMV DNA Polymerase Activity

To directly test the effect of leflunomide on viral DNA polymerase, specific enzyme activity was quantitated by biochemical assay. Crude protein extracts prepared from CMV-infected HUVEC or HFF, or from uninfected control cells, were reacted with activated (partially single-stranded) template DNA, dATP, dGTP, dCTP, and [$^3$H]TTP in high salt buffer (inhibitory for mammalian but not CMV DNA polymerase) in the presence or absence of various concentrations of A771726 or PFA. Radiolabel incorporation into template DNA was measured by β-scintillation counting, and these values were used to determine specific enzyme activity as a function of reaction time and total protein concentration of extracts.

HUVEC were inoculated with CMV strain VHL/E or BUR/E, and HFF were inoculated with CMV strain P8. Cultures were incubated until ~100% infection was achieved as determined by cytopathic change, harvested by brief trypsin digestion, washed twice in PBS, and pelleted by centrifugation. The CMV-specific DNA polymerase assay protocol was based on previously described methods. Cell pellets (~2×10$^6$ cells) were suspended in 0.5 ml extraction buffer (50 mM Tris-HCl [pH 8.0], 3 mM dithiothreitol, 200 mM KCL, 2 mM ATP, 2 mM MgCl$_2$, 0.2 mM PMSF, and 10% (v/v) glycerol), and disrupted by sonication. The resulting homogenates were clarified by centrifugation. Each DNA polymerase reaction mixture contained in a total volume of 100 μl: 50 mM Tris-HCl (pH 8.0), 150 mM KCl, 4 mM MgCl$_2$, 8 ug bovine serum albumin, 1 mM dithiothreitol, 2.25% (v/v) glycerol, 100 uM each of dATP, dCTP, dGTP, 1.712 uM [$^3$H]dTTP, 14.6 ug of activated calf thymus DNA, 10 ul of CMV-infected or uninfected cell lysate, and various concentrations of A771726 or phosphoformate (PFA) (3 replicate reactions/concentration). Each experiment also included time$_0$ controls and measurement of total available radiolabel. Assays were incubated for 1 hour at 37° C. in round-bottom microtiter plates, then harvested onto 96-well Unifilter-GF/C filter plates (Packard, Meriden Conn.) and immediately terminated by three washes with cold 5% TCA/1% sodium pyrophosphate. Wells used to measure total available label were not washed. Filter plates were dried following a final ethanol wash, supplied with 25 μl/well Microscint 20 scintillation cocktail (Packard), and counted on a microplate scintillation counter (Top-Count, Packard). Polymerase specific activity was expressed as radiolabel incorporation rate per mg of cell lysate total protein (assayed by BioRad method).

Figure 4:
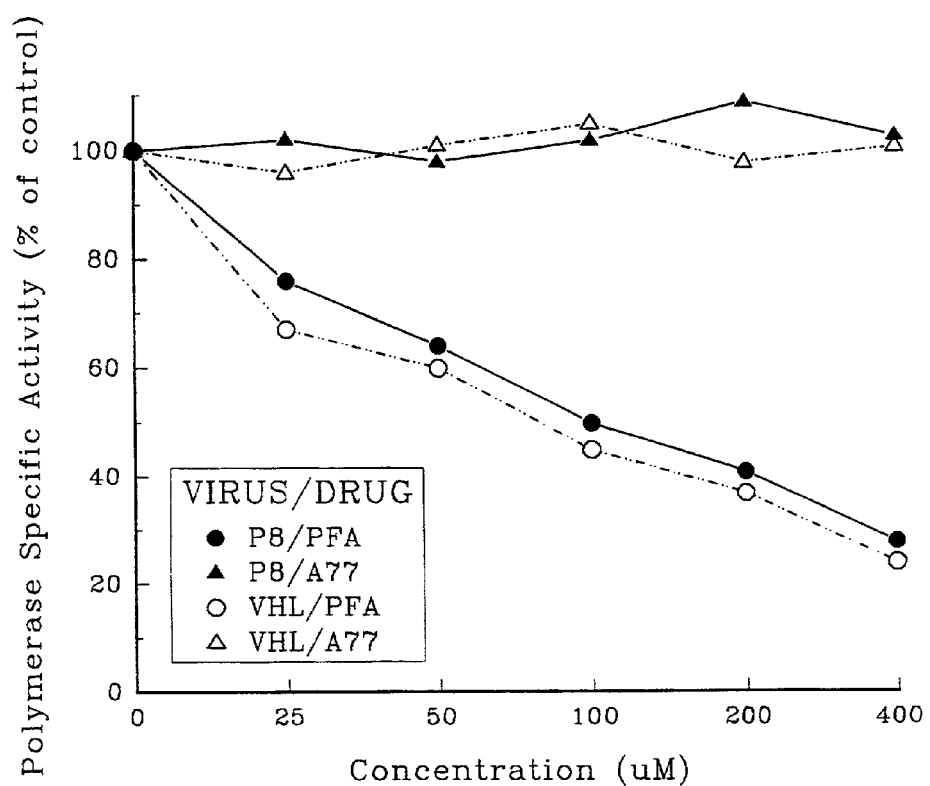
FIG. 4 displays data from a biochemical assay of CMV DNA polymerase activity in CMV-infected cells, in the presence of various concentrations of A771726.
Figure 5:
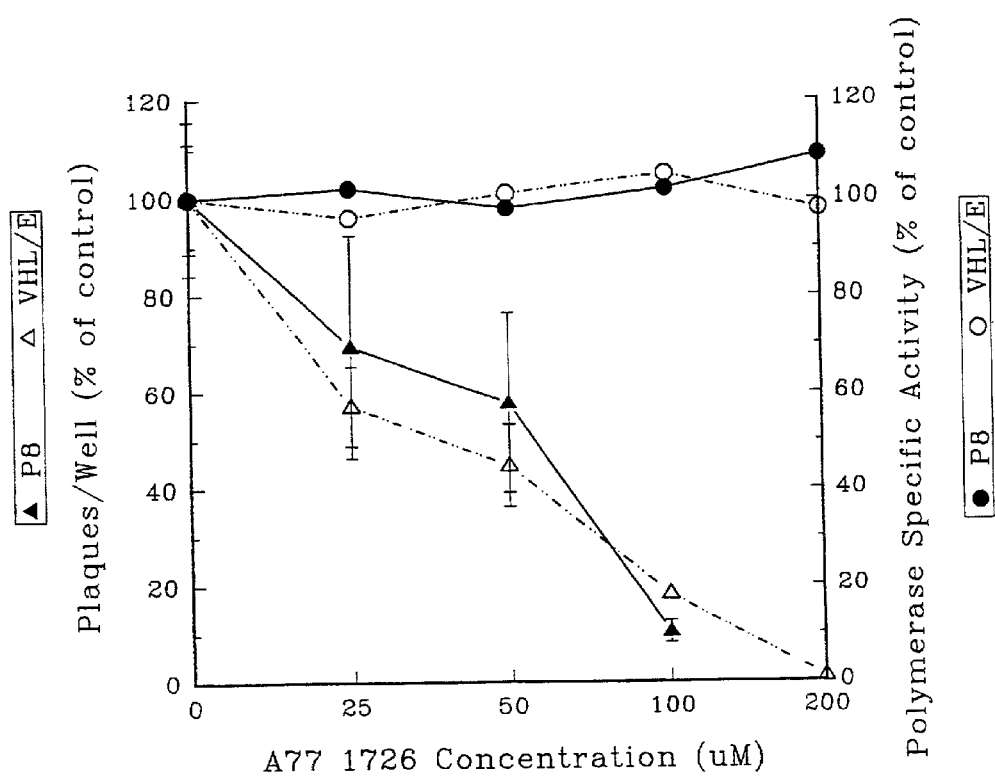
FIG. 5 displays the superimposition of plaque assay data and polymerase assay data and further shows the lack of effect of A771726 on CMV DNA polymerase activity even at concentrations that maximally inhibit CMV plaque formation.

While uninfected cell extracts inhibited no detectable enzyme activity, extracts derived from CMV-infected cells assayed in the absence of A771726 or PFA exhibited specific viral DNA polymerase activities in the range of 276-379 nM incorporation/hr/mg protein. Representative results of experiments performed with extracts of VHL/E-infected HUVEC or P8-infected HFF (2-4 replicate experiments per virus/cell combination) are presented in FIG. 4. Data shown in FIG. 5, (specific enzyme activity expressed as percent of PFA/A771726-free controls), demonstrate that, while PFA reduced viral DNA polymerase activity in a concentration-dependent manner (with complete inhibition at 1 mM). A771726 showed no detectable inhibitory activity even at concentrations which dramatically reduced plaque formation (FIG. 5). Experiments performed with extracts prepared from CMV strain BUR/E-infected HUVEC generated essential identical results.

EXAMPLE 5

Effect of Leflunomide Product on Virion Assembly

Transmission electron microscopy was employed to directly examine virion morphology within A771726-treated or untreated CMV-infected HUVEC. HUVEC monolayers in 6-well culture plates were inoculated with CMV strain VHL/E (1.0 PFU/cell) in the presence or absence of 200 μM A771726 as described above, and incubated for 4-7 days. Cells were harvested by brief trypsin digestion, washed twice in PBS, then fixed by the addition of 1 ml 2% phosphate buffered gluteraldehyde and again pelleted by centrifugation. Specimens were post-fixed in 1% phosphate buffered osmium tetroxide (1 hour), then dehydrated in graded ethanol washes. Specimens were embedded in Spur low viscosity embedding media (SEM). Blocks were cured for a minimum of 12 hours at 70° C. Thin sections (approximately 100 nm) were cut from cured blocks using an ultramicrotome (LKB Nova), and mounted on 2-mm 200 mesh copper grids. Grids were heavy metal-stained using a standard two-step uranyl acetate/lead citrate technique, then examined and photographed at. 80 kV with a Zeiss EM900 transmission electron microscope by an individual with no knowledge of the nature of the investigation.

Typical naked herpes-type viral capsids measuring approximately 100 nM in diameter are visible within the nuclei of infected cells, with no apparent differences in capsid quantity or morphology between A771726-treated and untreated cells. This implies that neither nucleocapsid assembly nor viral DNA packaging are impeded by leflunomide. However profound differences emerged within the cytoplasm of these cells. While tegument and external membrane were acquired normally in untreated cells resulting in the appearance of complete virions measuring just over 200 nM, viral particles appeared not to have matured far beyond the 100 nM naked capsid stage in the presence of A771726. In addition, dense bodies, amorphous cytoplasmic viral protein accumulations consisting primarily of pp65, clearly appear membrane-bound in untreated cells, but not in A771726-treated cells. The significance of this latter observation is not clear, but may represent an additional A771726-mediated defect in organization of virion components.

EXAMPLE 6

Effectiveness of Leflunomide Product Against Drug-resistant CMV

Figure 6:
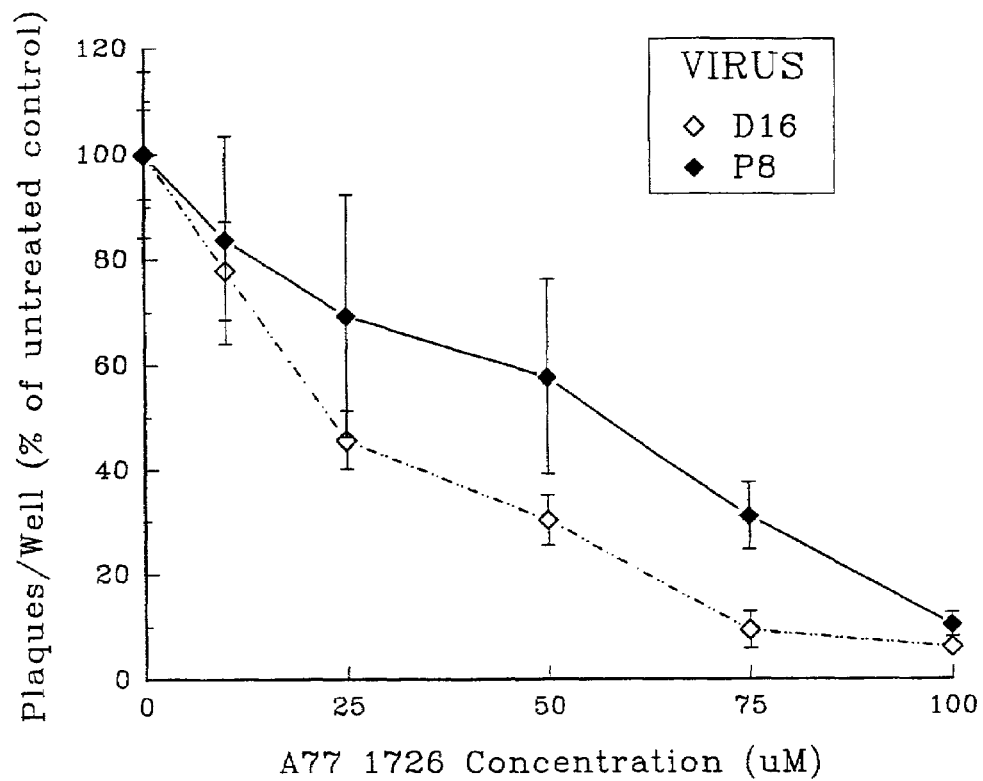
FIG. 6 displays plaque assay data demonstrating the equivalent sensitivity of drug-sensitive CMV strain P8 and multidrug-resistant CMV strain D16 to the anti-viral effect of A771726.

All current anti-CMV chemotherapies focus upon inhibition of viral DNA replication, although specific mechanisms vary slightly among different agents. Clinical strains have emerged which exhibit cross-resistance to multiple drugs. The effect of leflunomide product on activity of drug-resistant virus was evaluated as follows. CMV strain D16 was isolated from the same patient as strain P8. However, unlike P8, D16 exhibits multi-drug resistance. Plaque reduction assays performed in HFF cultures as described above (results shown in FIG. 6) revealed equivalent sensitivity of these two isolates to A771726 ($ID_{50}$~40-60 µM). Thus leflunomide-mediated inhibition of viral activity occurs independent of resistance to current clinical chemotherapeutic agents.

EXAMPLE 7

Anti-viral Activity of Leflunomide in vivo

Figure 7:
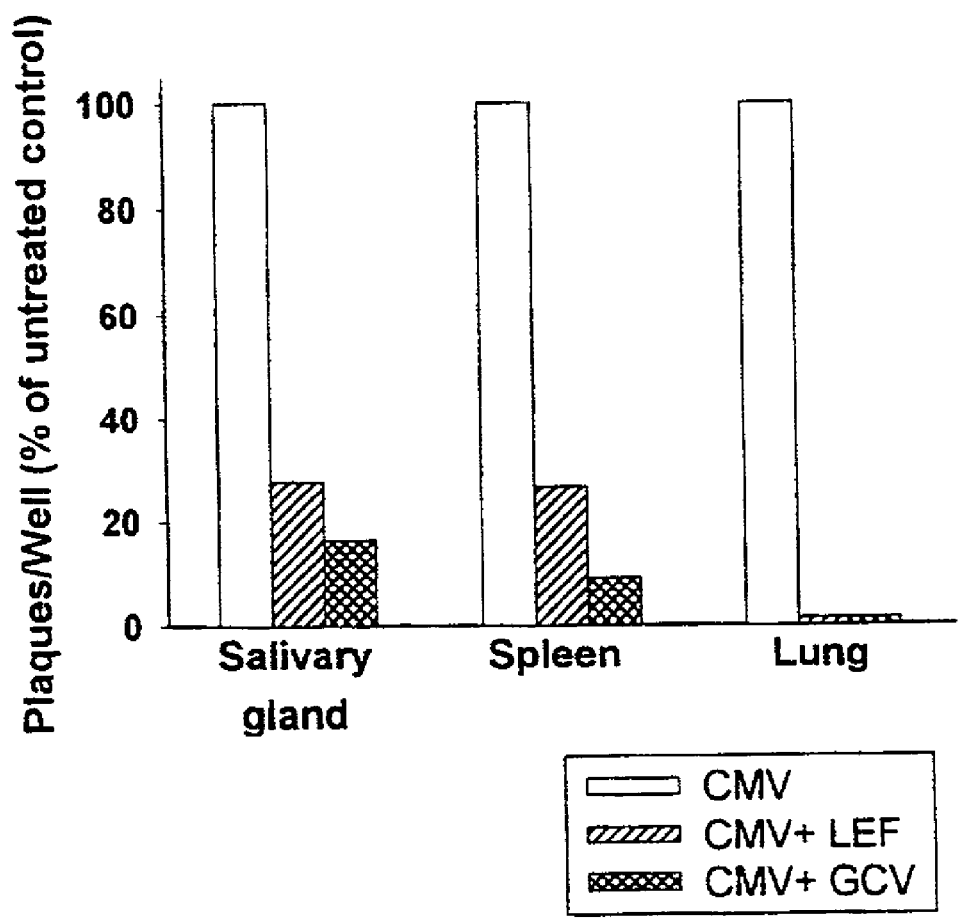
FIG. 7 displays plaque assay data from tissues of one representative animal challenged with CMV and treated with leflunomide.

To determine the effectiveness of leflunomide in the control of viral load in vivo, immunodeficient nude rats were inoculated intraperitoneally with rat CMV (RCMV RA67, Maastricht strain; Bruggeman et al., Arch. Virol, 76:189, 1983) at a challenge dose of $10^5$ PFU/animal, and treated with leflunomide (15 mg/kg/day for 14 days), ganciclovir (10 mg/kg/day for 5 days), or an equal volume of vehicle (1% methylcellulose) (3 animals/group). The experiment also included uninfected negative controls. At 14 days post-inoculation, rats were euthanized and salivary glands, lungs, and spleens were harvested for assay. Portions of tissues were sectioned and stained for histologic examination. The remainder of each was homogenized and assayed for virus yield by plaque assay on rat embryo fibroblast monolayers. Successful infection of the animals was demonstrated by the presence of classic cytomegalic glandular epithelial cells, by immunohistochemical verification of the intracellular expression of RCMV proteins, and by the recovery of infectious virus in plaque assays. Furthermore, leflunomide treatment indeed reduced the accumulation of RCMV in all three tissues. Data generated by plaque assay of tissue homogenates prepared from one representative animal of each treatment group are shown in FIG. 7, normalized to RCMV-infected, non-treated control. Although absolute PFU values derived from infected, untreated animals varied considerably between salivary gland ($1.0 \times 10^6$ PFU/gm) and lung and spleen ($3.4 \times 10^3$ PFU/gm, $1.5 \times 10^3$ PFU/gm, respectively), in all cases leflunomide significantly reduced viral load in inoculated animals.

Leflunomide showed a significant in vivo anti-viral effect in this initial experiment despite the fact that the dosing schedule was clearly sub-optimal. Following administration at 15 mg/kg, serum concentration of A771726 peaks at ~280 µM, dropping to sub-therapeutic levels by 6 hours, and ultimately to a 24-hour trough of <10 µM. Data from in vitro studies has shown that 10 µM has little if any antiviral effect (see FIG. 1). Thus, further experiments using a more frequent dosing regimen are expected to show an even better anti-viral effect.

EXAMPLE 8

Anti-viral Activity of Leflunomide Product Against HSV

A. Effect on Production of Infectious Virus

Figure 8:
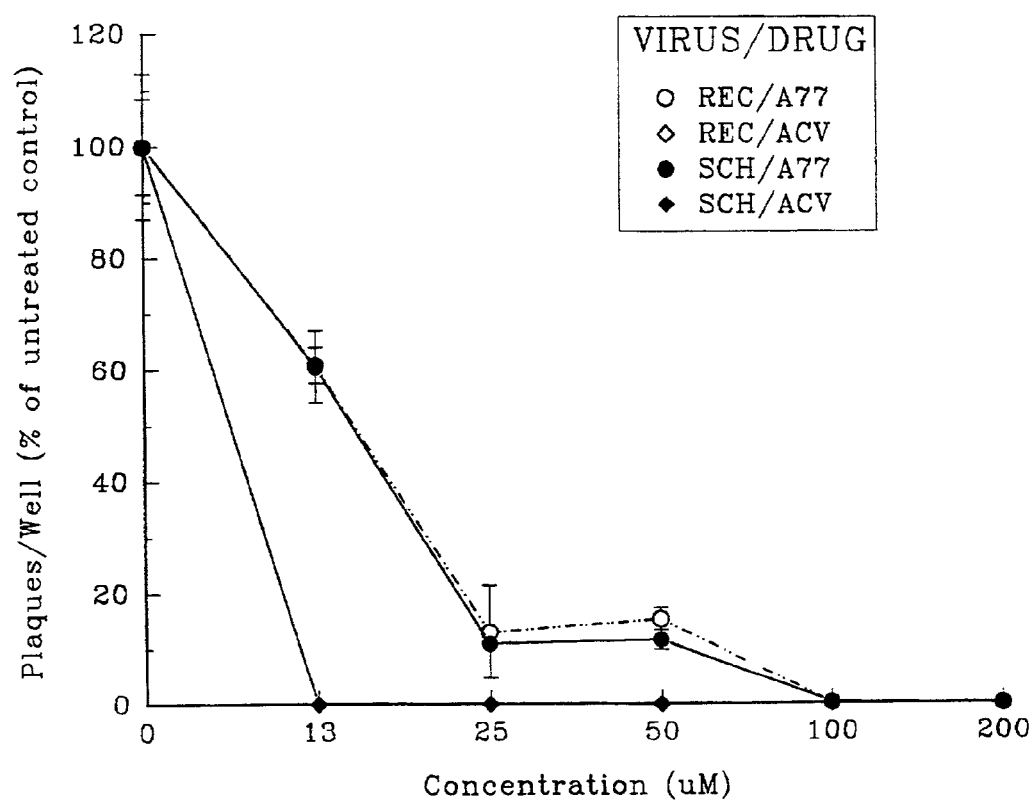
FIG. 8 displays plaque assay data demonstrating activity of A771726 against HSV.

To determine the impact of leflunomide product upon production of infectious HSV, plaque assays (as described in Example 1) were performed with HSV strain KOS, as well as with 4 individual fresh clinical HSV isolates, in both VERO cells and HUVEC, substituting acyclovir (ACV) for ganciclovir as the positive control for viral inhibition. Data generated by assay of 2 isolates (REC, SCH) in VERO cells presented in FIG. 8 demonstrate that the activity of A771726 against HSV in similar to that observed against CMV. Studies of all HSV isolates generated similar results in both VERO cells and HUVEC.

B. Effect of Leflunomide Product on HSV DNA Polymerase Activity

Figure 9:
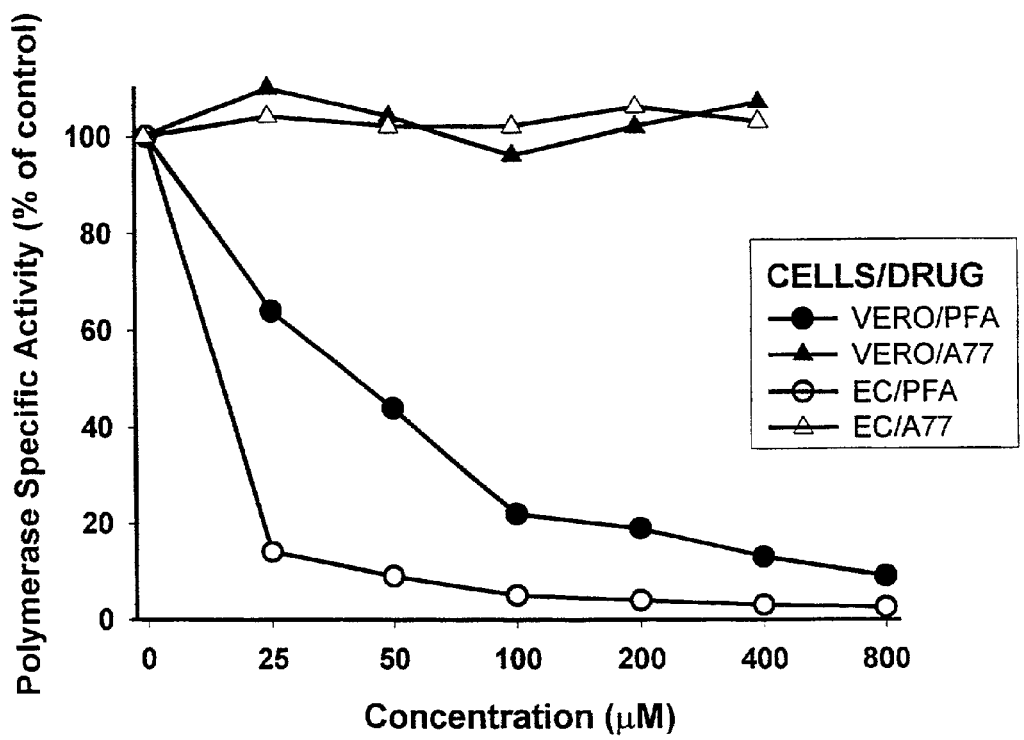
FIG. 9 displays data from a biochemical assay of HSV DNA polymerase activity in HSV-infected cells

To directly test the effect of leflunomide on HSV DNA polymerase, specific enzyme activity was quantitated by biochemical assay as described in Example 4B. Results representative of studies of all HSV isolates in both VERO cells and HUVEC are presented in FIG. 9. As was observed in CMV experiments (Example 4B), A771726 had no detectable inhibitory effect upon HSV DNA polymerase activity.

C. Effect of Leflunomide Product on Virion Assembly

Transmission electron microscopy (as described in Example 5) was employed to directly visualize virion morphology within A771726-treated or untreated HSV-infected HUVEC. Observations were very similar to those of CMV-infected cells. Specifically, in the presence of A771726, HSV nucleocapsids appear not to acquire tegument in the cytoplasmic phase of assembly.

EXAMPLE 9

Effect of Leflunomide Products on Various Viruses

The anti-viral activity of various leflunomide products was tested against a variety of viruses responsible for respiratory infections according to the following procedure.

The following leflunomide products were tested: A771726 (designated compound no. 99-125), N-(4-trifluoromethylphenyl)-3-methylisoxazol-4-carboxamide (designated compound no. 99-126) and N-(3-trifluoromethylphenyl)-5-methylisoxazol-4-carboxamide (designated compound no. 99-127).

Viruses were grown in suitable cell culture. Influenza A and B viruses were grown in Madin Darby canine kidney (MDCK) cells. Respiratory syncytial virus (RSV) (A2; ATCC) and parainfluenza type 3 virus (14702; clinical isolate from Hospital St. Justine, Montreal, Canada) were grown in African green monkey kidney (MA-104) cells. Measles virus (Chicago strain; CDC) was grown in African green monkey kidney (CV-1) cells. Adenovirus type 1 (65089/Chicago) was grown in human lung carcinoma (A549) cells.

Leflunomide products were tested for inhibition of viral cytopathic effect (CPE) as follows, generally as described in Barnard et al., Antiviral Chem. Chemother., 8:223-233, 1997 and Huffman et al., Antiviral Chem. Chemother., 8:75-83, 1997). The test is run in 96-well flat-bottomed microtiter plates. Seven one-half $\log_{10}$ dilutions of each test compound was added to the cell monolayer; within 5 minutes, the virus is added and the plate is sealed and incubated at 37° C. The CPE is read microscopically when untreated infected control cells develop a 3 to 4+CPE (approximately 72 to 96 hours). A known positive control drug is evaluated in parallel with the test drugs. The positive control drug is ribavirin for influenza, measles, RSV and parainfluenza viruses, and the positive control is (S)-1-(3-hydroxy-2-phosphonylmethoxyprophyl) adenine (HPMPA) for adenovirus. The data are shown below in Table 1 expressed as 50% effective virus-inhibitory concentrations (EC50).

A further test measuring neutral red dye uptake is run to validate the CPE inhibition seen in the initial test generally according to McManus, *Appl. Environment. Microbiol.*, 31:35-38, 1976). The test utilizes the same 96-well plates after the CPE has been determined. Neutral red is added to the medium in each well; cells not damaged by virus take up a greater amount of dye, which is determined spectrophotometrically on a computerized autoreader. Another EC50 value is determined from the dye uptake test.

Compounds considered active by both CPE inhibition and NR dye uptake are evaluated for reduction of virus yield using the same 96-well plates. The virus titer remaining in frozen and thawed eluates from each well is determined by serial dilution onto monolayers of susceptible cells and observing development of CPE in these cells (which is an indication of presence of infectious virus). A known active drug is also run in parallel as a positive control. The data is used to calculate the 90% effective concentration (EC90), which is the test drug concentration that inhibits virus yield by 1 $\log_{10}$.

Cytotoxicity of each test compound is also evaluated as follows. In the initial CPE inhibition tests, two wells of uninfected cells treated with each concentration of test compound are run in parallel with the infected, treated wells. When the CPE is determined microscopically, the toxicity control cells are also examined microscopically for any changes in cell appearance compared to normal uninfected, untreated control cells. Changes, which may manifest as enlargement, granularity, ragged edges, filmy appearance, rounding, detachment from the surface of the well, or other changes, are given a designation of T (100% toxic), PVH (partially toxic-very heavy-80%), PH (partially toxic-heavy-60%), P (partially toxic-40%), PS (partially toxic-slight-20%) or 0 (no toxicity-0%) in accordance with the degree of cytotoxicity observed. A 50% cell inhibitory (cytotoxic) concentration (IC50) is determined by regression analysis of these data. A neutral red IC50 is also determined based on uptake of neutral red dye by the toxicity control cells.

The cytotoxic effect of compounds that are anti-virally active in both the CPE and neutral red tests is further quantitated as follows. Culture plates are seeded with cells (sufficient to be approximately 20% confluent in the well) and exposed to varying concentrations of the test drug while the cells are dividing rapidly. The plates are then incubated in a $CO_2$ incubator at 37° C. for 72 hours, neutral red is added, and the degree of color intensity indicating number of viable cells is determined spectrophotometrically. An IC50 is determined by regression analysis.

The activity of each compound is expressed as a selectivity index (SI), which is the IC50 or IC90 divided by the EC50. Generally, an SI of 10 or greater is considered indicative of good anti-viral activity, although other factors, such as a low SI for the positive control, are also considered.

Results are shown in Table 1 below and indicated that A771726 was highly active against both measles and rhinovirus. While the leflunomide products did not appear to be significantly active against RSV, other experiments in different systems have demonstrated that A771726 does have some anti-RSV activity.

TABLE 1

| test cpd | Virus | CPE Inhibition test | | | Neutral Red Uptake test | | |
|---|---|---|---|---|---|---|---|
| | | EC50 | IC50 | SI | EC50 | IC50 | SI |
| 99-125 | Influenza A (H1N1) with test drug | >20 | 29 | <1.4 | 63 | 63 | 1.0 |
| 99-125 | Influenza A (H1N1) with positive control drug | 5.8 | >100 | >17 | 5.6 | >100 | >18 |
| 99-125 | Influenza A (H3N2) with test drug | 63 | 30 | 0.5 | 63 | 69 | 1.1 |
| 99-125 | Influenza A (H3N2) with positive control drug | 5.2 | >100 | >19 | 5.4 | >100 | >19 |
| 99-125 | Influenza B with test drug | >200 | 50 | <0.2 | 60 | 65 | 1.1 |
| 99-125 | Influenza B with positive control drug | 2.8 | >100 | >36 | 4.6 | >100 | >22 |
| 99-125 | Adenovirus Type 1 with test drug | >1000 | 560 | 0 | 560 | 580 | 1 |
| 99-125 | Adenovirus Type 1 with positive control drug | 39 | 310 | 8 | 23 | >460 | >20 |
| 99-125 | Measles Virus with test drug | <1 | >660 | >560 | <1 | >100 | >100 |
| 99-125 | Measles Virus with positive control drug | 41 | 2290 | 56 | 41 | 2000 | 49 |
| 99-125 | Parainfluenza Type 3 Virus with test drug | 60 | 30 | 0 | 70 | 50 | 0 |
| 99-125 | Parainfluenza Type | 230 | 2290 | 10 | 120 | 4100 | 33 |

TABLE 1-continued

| test cpd | Virus | CPE Inhibition test | | | Neutral Red Uptake test | | |
|---|---|---|---|---|---|---|---|
| | | EC50 | IC50 | SI | EC50 | IC50 | SI |
| 125 | 3 Virus with positive control drug | | | | | | |
| 99-125 | Respiratory Syncytial Virus A with test drug | 60 | 20 | 0 | 200 | 143 | 0 |
| 99-125 | Respiratory Syncytial Virus A with positive control drug | 290 | 2310 | 8 | 82 | 2700 | 33 |
| 99-125 | Rhinovirus Type 5 with test drug | 10 | 1000 | 100 | 10 | 500 | 50 |
| 99-125 | Rhinovirus Type 5 with positive control drug | <0.27 | 217 | >803 | <0.27 | >270 | >1000 |
| 99-126 | Influenza A (H1N1) with test drug | >20 | 63 | <3.2 | 48 | 48 | 1.0 |
| 99-126 | Influenza A (H1N1) with positive control drug | 5.8 | >100 | >17 | 5.6 | >100 | >18 |
| 99-126 | Influenza A (H3N2) with test drug | >200 | 72 | 0 | 30 | 30 | 1.0 |
| 99-126 | Influenza A (H3N2) with positive control drug | 5.2 | >100 | >19 | 5.4 | >100 | >18 |
| 99-126 | Influenza B with test drug | 60 | 72 | 1.2 | 46 | 46 | 1.0 |
| 99-126 | Influenza B with positive control drug | 2.8 | >100 | >36 | 4.6 | >100 | >22 |
| 99-126 | Adenovirus Type 1 with test drug | >100 | 60 | 0 | >100 | 60 | 0 |
| 99-126 | Adenovirus Type 1 with positive control drug | 39 | 310 | 8 | 23 | >460 | >20 |
| 99-126 | Measles Virus with test drug | 10 | 60 | 6 | 14 | 25 | 2 |
| 99-126 | Measles Virus with positive control drug | 41 | 2290 | 56 | 41 | 2000 | 49 |
| 99-126 | Parainfluenza Type 3 Virus with test drug | >100 | 11 | 0 | 20 | 20 | 1 |
| 99-126 | Parainfluenza Type 3 Virus with positive control drug | 230 | 2290 | 10 | 120 | 4100 | 33 |
| 99-126 | Respiratory Syncytial Virus A with test drug | >100 | 40 | 0 | >100 | 30 | 0 |
| 99-126 | Respiratory Syncytial Virus A with positive control drug | 290 | 2310 | 8 | 82 | 2700 | 33 |
| 99-126 | Rhinovirus Type 5 with test drug | 100 | 100 | 1 | >100 | >100 | 0 |
| 99-126 | Rhinovirus Type 5 with positive control drug | <0.27 | 217 | >803 | <0.27 | >270 | >1000 |
| 99-127 | Influenza A (H1N1) with test drug | >200 | >200 | 0 | 66 | 66 | 1.0 |
| 99-127 | Influenza A (H1N1) with positive control drug | 5.8 | >100 | >17 | 5.6 | >100 | >18 |
| 99-127 | Influenza A (H3N2) with test drug | >200 | 63 | 0 | 46 | 46 | 1.0 |
| 99-127 | Influenza A (H3N2) with positive control drug | 5.2 | >100 | >19 | 5.4 | >100 | >18 |
| 99-127 | Influenza B with test drug | >200 | >200 | 0 | 47 | 60 | 1.1 |
| 99-127 | Influenza B with positive control drug | 2.8 | >100 | >36 | 4.6 | >100 | >22 |
| 99- | Measles Virus with | >100 | 60 | 0 | >100 | 30 | 0 |

TABLE 1-continued

| test | | CPE Inhibition test | | | Neutral Red Uptake test | | |
|---|---|---|---|---|---|---|---|
| cpd | Virus | EC50 | IC50 | SI | EC50 | IC50 | SI |
| 127 | test drug | | | | | | |
| 99-127 | Measles Virus with positive control drug | 41 | 2290 | 56 | 41 | 2000 | 49 |
| 99-127 | Parainfluenza Type 3 Virus with test drug | >100 | 20 | 0 | >100 | 15 | 0 |
| 99-127 | Parainfluenza Type 3 Virus with positive control drug | 230 | 2290 | 10 | 120 | 4100 | 33 |
| 99-127 | Respiratory Syncytial Virus A with test drug | >100 | 30 | 0 | >100 | 20 | 0 |
| 99-127 | Respiratory Syncytial Virus A with positive control drug | 290 | 2310 | 8 | 82 | 2700 | 33 |

Compounds 99-125, -126 and -127 were tested against HSV-1, HSV-2 and hCMV using a similar protocol, except that drug is added one hour (instead of 5 minutes) prior to infection so that the assay system can detect inhibitors of early replicative steps such as adsorption or penetration as well as later events. In the assays, at least six drug concentrations were used ranging from 100 µg/ml to 0.03 µg/ml in 5-fold increments and the data were used to calculate the drug dose that inhibits viral replication by 50% (EC50). A cytotoxic concentration 50 (CC50) was also calculated using neutral red dye uptake. Compound 99-125 (A771726) showed good activity against human CMV but not HSV-1 and HSV-2. The difference between these results and the results with respect to HSV described in Example 8 above is explained by the fact that this protocol only evaluated CPE, rather than virus yield from the inoculated cultures, and may have used higher inoculating titers. Although A771726 appears to inhibit viral nucleocapsid tegumentation, dramatically attenuating the production of complete infectious virions by infected cells, it prevents neither the entry of the primary inoculum into host cells nor the development of morphologic cytopathic changes within infected cells. Thus, especially following high titer inoculation, simple observation of CPE provides no indication of the extent of infectious virus output, and CPE could be observed despite a reduction in virus yield provided by leflunomide product.

EXAMPLE 10

Effect of Leflunomide Products on Hepatitis B and C Viruses

The anti-viral effect of leflunomide products, alone and also in combination with uridine, on hepatitis B virus (HBV) was assayed as follows, generally according to Korna et al., *Antiviral Res.*, 217:217, 1991.

Chronically HBV-producing 2.2.15 human liver cells (Aos et al., *Proc. Nat'l Acad Sci.*, 84:4641, 1987) were seeded into 24-well tissue culture plates and grown to confluence. Test compounds were added daily for a continuous 9 day period and culture medium was changed daily during the treatment period. Culture medium was collected and stored for analysis of extracellular (virion) HBV DNA after 0, 3, 6 and 9 days of treatment. Treated cells were lysed 24 hours following day 9 of treatment for analysis of intracellular HBV genomic DNA. HBV DNA was then analyzed in a quantitative and qualitative manner for overall levels of HBV DNA (both intracellular and extracellular DNA levels) and relative rate of HBV replication (indicated by intracellular DNA levels).

HBV DNA was assayed using blot hybridization techniques (Southern and slot blot) and $^{32}$P-labelled HBV-specific probes. HBV DNA levels were determined by comparison to known amounts of HBV DNA standards applied to every nitrocellulose membrane (gel or slot blot). An AMBIS beta scanner was used to measure radioactive decay of the hybridized probes directly from the nitrocellulose membrane. Standard curves generated by multiple analyses were used to correlate cpm measurements with relative levels of target HBV DNA. The levels of extracellular HBV virion DNA were analyzed by slot blot hybridization. The effect of drug treatment was evaluated by comparing HBV DNA levels to levels at day 0. The replication status of the HBV was determined by quantitating levels of HBV DNA in each of the three classes of viral genomic forms (episomal monomers, DNA replication intermediates and integrated HBV DNA). The levels of replication intermediates and episomal monomers were used as an indicator of the relative level of HBV replication, while the levels of integrated HBV DNA were used to normalize the relative amounts of DNA in each lane (integrated HBV DNA would be expected to remain constant on a per cell basis).

Toxicity of test compounds to cultures of 2.2.15 cells was also determined as follows. Four concentrations of each compound were assayed and compared to untreated control cultures. Toxicity was determined by the uptake of neutral red dye, as determined by absorbance at 510 nm relative to untreated cells.

Results are shown in Table 2 below and indicate that A771726 and N-(4-trifluoromethylphenyl)-3-methylisoxazol-4-carboxamide have some anti-viral effect on HBV, which is increased when the leflunomide product is combined with uridine.

TABLE 2

| Compound | EC50 | EC90 | CC50 | SI |
|---|---|---|---|---|
| 99-125 | >100 | >100 | 71 | ND |
| 99-126 | >100 | >100 | 110 | ND |
| 99-127 | 11 | 96 | 67 | 0.7 |
| 99-125 with uridine | 34 | 337 | 78 | 0.2 |

TABLE 2-continued

| Compound | EC50 | EC90 | CC50 | SI |
| --- | --- | --- | --- | --- |
| 99-126 with uridine | 4.3 | 73 | 99 | 1.4 |
| 99-127 with uridine | 4.2 | 31 | 84 | 2.7 |
| uridine alone | >100 | >100 | >100 | ND |

In addition, clinical treatment of a human patient suffering from chronic hepatitis C infection with leflunomide (HWA-486) resulted in a decrease in the patient's CMV viral load. The patient is a 62 year old white male who received a liver transplant in January 1990 for hepatitis C. Over the following nine years he developed indolent hepatitis C with mildly elevated liver enzymes. Because of slowly progressive kidney impairment, presumably related to a combination of chronic hepatitis C and long term cyclosporine A treatment, he was started on leflunomide treatment. A liver biopsy at the time of initiation of leflunomide showed moderate fibrosis and mild portal inflammation consistent with chronic hepatitis C. After an initial leflunomide loading dose of 300 mg daily for two days, a maintenance dose of 50 mg daily was started.

His blood levels of A771726 have gradually risen to 113 µg/ml. When his A771726 blood levels reached 40 µg/ml, his dose of cyclosporine was gradually reduced from 160 mg daily to 60 mg daily, and his 12 hour cyclosporine trough blood levels fell from 150 ng/ml at the initiation of therapy to 70 ng/ml at the time of repeat hepatitis C testing. His 10 mg daily dose of prednisone has not been changed.

As the new treatment regimen was implemented, his kidney function improved; his serum creatinine fell from 3.6 mg/dl to 2.2 mg/dl and his BUN fell from 94 mg/dl to 55 mg/dl. Just before leflunomide was begun his hepatitis C viral load in peripheral blood was 3,120,000 copies, measured by quantitative PCR (Quest Diagnostics). After six weeks of therapy with leflunomide, his hepatitis C viral load had fallen to 1,480,000 copies, measured by the same PCR methodology.

This data indicates that the leflunomide therapy was associated with a 50% drop in this patient's hepatitis C viral load.

Numerous modifications and variations in the practice of the invention are expected to occur to those skilled in the art upon consideration of the foregoing description of the presently preferred embodiments thereof Consequently, the only limitations which should be placed upon the scope of the present invention are those which appear in the appended claims.

What is claimed is:

1. A method of treating a patient suffering from a viral infection comprising administering to said patient a therapeutically effective amount of a leflunomide product and administering to said patient a pyrimidine compound in an amount effective to enhance serum levels of uridine, cytidine or thymidine.

2. The method of claim 1 wherein the leflunornide product is N-(4-trifluoromethylphenyl)-5-methylisoxazol-4-carboxamide (HWA 486).

3. The method of claim 1 wherein the leflunomide product is N-(4-trifluoromethylphenyl)-2-cyano-3-hydroxycrotonamide (A771726).

4. The method of claim 1 wherein the leflunomide product is an amide of a malononitrile.

5. The method of claim 1 wherein the pyrimidine is uridine, orotic acid or orotidine.

6. The method of claim 1, 2, 3 or 4 wherein the virus is a herpesvirus.

7. The method of claim 1, 2, 3 or 4 wherein the virus is selected from the group consisting of paramyxoviruses, picomaviruses, hepatitis viruses, CMV, HSV, measles virus, rhinovinuses, hepatitis B and hepatitis C.

8. The method of claim 1 or 5 wherein the leflunomide product is a compound of formula:

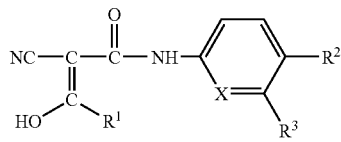

(II)

wherein
R¹ denotes
a) methyl,
b) $(C_3-C_6)$-cycloalkyl,
c) $(C_2-C_6)$-alkyl, having at least 1 triple or double bond between the carbon atoms,
R² denotes
a) —CF₃ or
b) —CN,
R₃ denotes
a) $(C_1-C_4)$-alkyl or
b) hydrogen atom, X denotes
a) —CH— group or
b) nitrogen atom,
the compound being present as such or in the form of a physiologically tolerable salt.

9. The method of claim 4 wherein the pyrimidine is uridine, orotic acid or orotidine.

10. The method of claim 1 or 5 wherein the teflunornide product is a compound of formula I or II:

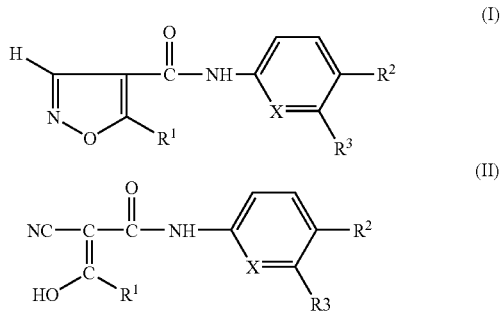

wherein in formula I or II
R¹ denotes
a) methyl,
b) $(C_3-C_6)$-cycloalkyl,
c) $(C_2-C_6)$-alkyl, having at least 1 triple or double bond between the carbon atoms,
R₂ denotes
a) —CF₃ or
b) —CN,
R³ denotes
a) $(C_1-C_4)$-alkyl or
b) hydrogen atom, and
X denotes
a) —CH-group or
b) nitrogen atom;
the compound being present as such or in the form of a physiologically tolerable salt.

11. A method of treating a patient suffering from a viral infection comprising administering to said patient (a) a therapeutically effective amount of a leflunomide product and (b) a pyrimidine compound without antiviral activity.

* * * * *